(12) United States Patent
Solina

(10) Patent No.: US 10,522,861 B2
(45) Date of Patent: Dec. 31, 2019

(54) ELECTROACTIVE CULTURES AND APPARATUSES THEREFOR

(71) Applicant: MICROrganic Technologies Inc., Castelton-On-Hudson, NY (US)

(72) Inventor: Brent A. Solina, Orchard Park, NY (US)

(73) Assignee: MICROrganic Technologies Inc., Castelton-On-Hudson ( * ) Notice: Subject to any disclaimer, the term of this patent is extended or adjusted under 35 U.S.C. 154(b) by 0 days.

(21) Appl. No.: 15/830,580

(22) Filed: Dec. 4, 2017

(65) Prior Publication Data
US 2018/0191015 A1    Jul. 5, 2018

Related U.S. Application Data

(63) Continuation of application No. 14/776,196, filed as application No. PCT/US2014/023185 on Mar. 14, 2014, now Pat. No. 9,837,677.
(Continued)

(51) Int. Cl.
*H01M 8/16* (2006.01)
*C12N 1/20* (2006.01)
(Continued)

(52) U.S. Cl.
CPC .............. *H01M 8/16* (2013.01); *C02F 3/005* (2013.01); *C12N 1/20* (2013.01); *G01N 27/447* (2013.01); *C02F 3/345* (2013.01); *C02F 3/346* (2013.01); *C02F 2103/06* (2013.01); *C02F 2103/28* (2013.01); *C02F 2103/32* (2013.01); *C02F 2209/05* (2013.01); *C02F 2209/06* (2013.01); *C02F 2209/22* (2013.01); *C02F 2209/24* (2013.01); *C02F 2209/36* (2013.01); *Y02E 60/527* (2013.01); *Y02P 70/56* (2015.11); *Y02W 10/37* (2015.05)

(58) Field of Classification Search
CPC ...................................................... H01M 8/16
See application file for complete search history.

(56) References Cited

U.S. PATENT DOCUMENTS

2004/0171139 A1    9/2004 Belcher et al.
2006/0011491 A1    1/2006 Logan et al.
(Continued)

OTHER PUBLICATIONS

Venkata Mohan et al., "Influence of anodic biofilm growth on bioelectricity production in single chambered mediatorless microbial fuel cell using mixed anaerobic consortia, Biosens Bioelectron." (Sep. 15, 2008, published online Mar. 21, 2008), vol. 24, No. 1, pp. 41-47.
(Continued)

*Primary Examiner* — Rosanne Kosson
(74) *Attorney, Agent, or Firm* — Heslin Rothenberg Farley & Mesiti P.C.

(57) ABSTRACT

Disclosed herein are methods, systems, and devices for generating electricity from an effluent source. In the presence of electrogenic bacteria and substrate electrodes, an electroactive biofilm is produced which possesses bioconductive capacity for efficiently producing an electric current while treating an effluent source such as, e.g., wastewater. This disclosure relates generally to the production of electricity from a biological source. In particular, this disclosure relates to microbial fuel cells (MFCs) and other bioelectrochemical systems (BES) that exploit an exogenous fuel source.

22 Claims, 8 Drawing Sheets

Related U.S. Application Data

(60) Provisional application No. 61/787,113, filed on Mar. 15, 2013.

(51) Int. Cl.
| | | |
|---|---|---|
| *G01N 27/447* | (2006.01) | |
| *C02F 3/00* | (2006.01) | |
| C02F 3/34 | (2006.01) | |
| C02F 103/06 | (2006.01) | |
| C02F 103/28 | (2006.01) | |
| C02F 103/32 | (2006.01) | |

(56) References Cited

U.S. PATENT DOCUMENTS

| | | |
|---|---|---|
| 2009/0324996 A1 | 12/2009 | Swift et al. |
| 2010/0279178 A1 | 4/2010 | Barkeloo et al. |
| 2011/0123876 A1 | 5/2011 | Vogel et al. |
| 2011/0139617 A1 | 6/2011 | Fransaer |
| 2012/0152835 A1 | 6/2012 | Cardenas et al. |

OTHER PUBLICATIONS

International Preliminary Report on Patentability for PCT/US2014/023185, dated Sep. 15, 2015.

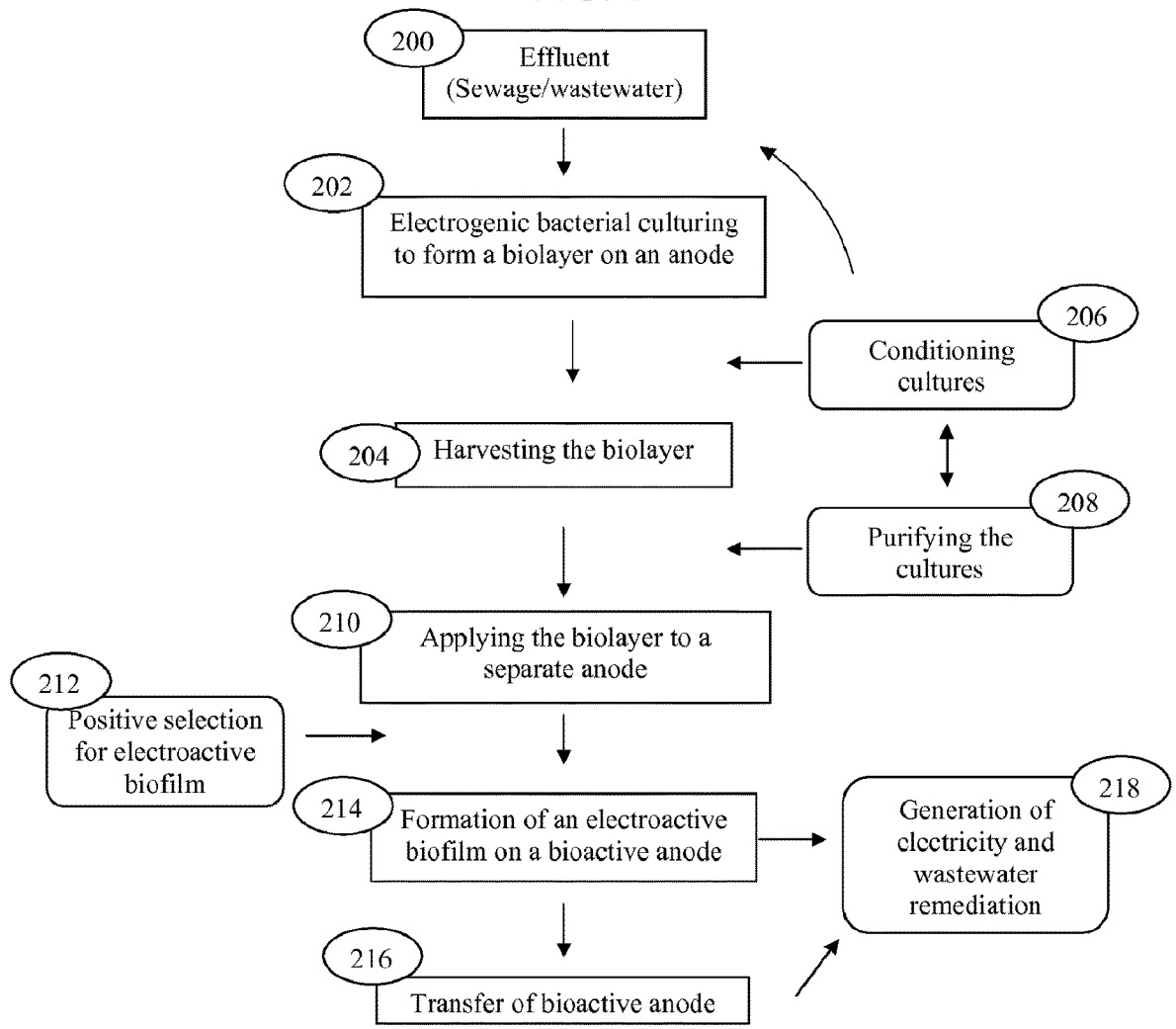

ELECTROACTIVE CULTURES AND APPARATUSES THEREFOR

CROSS-REFERENCE TO RELATED APPLICATIONS

This application is a continuation of U.S. patent application Ser. No. 14/776,196, filed Sep. 14, 2015, which is a U.S. National Phase filing under 35 U.S.C. § 371 of International Application No. PCT/US2014/023185, filed Mar. 11, 2014, which claims benefit of priority from U.S. Provisional Patent Application No. 61/787,113, filed Mar. 15, 2013, the entire contents of which are incorporated herein by reference.

TECHNICAL FIELD

This disclosure relates generally to the production of electricity from a biological source. In particular, this disclosure relates to microbial fuel cells (MFCs) and other bio-electrochemical systems (BES) that exploit an exogenous fuel source. Also included are systems and methods for generating electricity in concert with treating the fuel source.

BACKGROUND

The following description is provided to assist the understanding of the reader. None of the information provided or references cited is admitted to be prior art.

A fuel cell is an electrochemical unit that converts chemical energy into an electrical current. The electric current is generated through chemical reactions using an input source, i.e., a fuel, that is oxidized in the presence of an electron producing catalyst. The oxidation typically occurs at an anode proximal to an electrolyte medium. The electrons cannot pass through the electrolyte medium, and thus, are shunted through an electrical circuit, which generates an electrical current by the transfer of electrons from an anode to a cathode. The reaction products accordingly form at the cathode.

Fuel cells can operate continuously by maintaining a constant source of chemical reactants. As such, fuel cells are distinct from electrochemical batteries, which produce an electrical current from an internal-thermodynamically closed-system, because fuel cells require reactants from an external source that can be replenished, i.e., thermodynamically "open" systems. Such replenishable systems require an energy source and an oxidizing agent. For example, hydrogen fuel cells use hydrogen as the source and oxygen as an oxidizing agent. These fuel cells may use oxygen and a hydrocarbon, e.g., methane, methanol, ethanol, etc., as the oxidizing agent and the fuel source, respectively, which consequently produces water and carbon dioxide ($CO_2$) as the reaction products.

Microbial fuel cells (MFCs), on the other hand, require a biochemical source of fuel or energy, i.e., from a "biomass," to facilitate proliferation of electrogenic bacterial cultures. While biomasses can be present in a variety of sources, electrogenic cultures are nevertheless difficult to maintain insofar as such cultures possess disparate metabolic requirements compared to other microbial cultures, i.e., possessing non-electrogenic bacteria. Further complicating MFC operation is that, even when carefully controlled, electrogenic cultures typically fail to maintain surface electrode confluence which imparts decreased performance and efficiency. Accordingly, new MFC devices, methods and systems are needed in industries seeking to remediate source contamination while efficiently generating electricity.

SUMMARY

In one aspect, the present invention provides a method of producing an electroactive biofilm, including (a) culturing electrogenic bacteria to form a biolayer on a substrate, where the biolayer possess a bioconductance, (b) harvesting the biolayer, and (c) applying the biolayer to a surface to form the biofilm, where the biofilm possesses increased bioconductance compared to the bioconductance of the biolayer. In some embodiments, the methods further include conditioning the bacteria, the biolayer or the biofilm, or any combination thereof, where the conditioning enhances the bioconductivity compared to the bioconductivity in the absence of the conditioning. In some embodiments, the conditioning is selected from introducing mediators, $CaCl_2$, sulfur, cell growth media, cell proliferation factors, adherence factors, cell viability factors, or increasing bacterial cell density or confluence, or any combination thereof.

In illustrative embodiments, mediators are quorum-sensing inducers selected from N-Acyl Homoserine Lactones (AHL) and AI-2 autoinducers, or both. In some embodiments, the methods further include preserving the biolayer or the biofilm, or both, where the preservation is selected from freezing, flash freezing in liquid nitrogen, slow freezing in the presence of glycerol, glycerine-base preservation, desiccation, and chemical preservation, or any combination thereof. In some embodiments, the surface is a catalyzed electrode surface. In suitable embodiments, the catalyzed electrode surface is nitrogen-doped carbon mesh. In some embodiments, the surface is composed of one or more materials selected from carbon mesh, carbon paper, carbon felt, carbon powder, carbon foam, carbon cloth, graphite felt, nitrogen-doped carbon, and/or corrosion resistant metals.

The corrosion resistant metals are selected from stainless steel, titanium, copper, silver, zinc, magnesium, iron, gold, aluminum, aluminum nitride, aluminum oxide, brass, cobalt, graphite, and beryllium, or any combination thereof in certain embodiments. In some embodiments, the surface substantially envelops a second substrate. In various embodiments, the second substrate is an electrode, such as an anode or a cathode. In some embodiments, the electrode is an anode. The second substrate is in fluid communication with an electrochemical complex capable of generating an electric current in the presence of electrons according to suitable embodiments of the present invention. In some embodiments, the electrochemical complex is a microbial fuel cell.

In suitable embodiments, the biofilm is capable of degrading organic constituents from a source to provide the electrons. The source, in some embodiments, is an effluent source selected from groundwater, contaminated groundwater, wastewater, sewage, landfill leachate, sugar refinery waste, paper pulping waste, bakery waste, brewery waste, and fluid compositions comprising bacterial factors, or any combination thereof. In illustrative embodiments, the bacterial factors are selected from divalent metal cations, one or more metals, iron, manganese, sulfites, phosphorus, calcium, and one or more proteins, or any combination thereof. In some embodiments, the second substrate is a bioactive anode configured for use in one or more microbial fuel cells, while in other embodiments the second substrate is a bioactive anode configured for transport to a microbial fuel cell system.

The applying is selected from cell-printing, piezoelectric printing, coated rolling, roll-to-roll conveying, spray nozzle application, electroactive deposition, magnetoactive deposition, laser induction, and biological laser printing, or any combination thereof in accordance with certain embodiments. In some embodiments, the methods further include monitoring one or more culturing factors, where the culturing factors are selected from pH, oxygen concentration, carbon dioxide levels, nitrogen levels, salinity, bacterial density, colony confluence, and voltage potential, or any combination thereof. In particular embodiments, the voltage potential is from about −5V to about 5V. In some embodiments, the methods further include regulating gas concentration, where the gas is oxygen.

The regulating in suitable embodiments is by diffusion though an elastomeric polymer selected from polydimethylsiloxane (PDMS) or polytetrafluoroethylene (PTFE), or both. In some embodiments, the regulating is by advective flow. In some embodiments, the methods further include stimulating one or more of the electrogenic bacteria, the biolayer, and/or the biofilm. In illustrative embodiments, the stimulating is selected from photostimulation, solar stimulation, application of concentrated wavelengths, irradiation, nuclear radiation, and ionizing radiation, or any combination thereof. The methods further include, in various embodiments, adding growth media, replenishing growth media, or homogenizing growth cultures, or any combination thereof. In some embodiments, one or more steps are performed in the presence of bacterial growth media.

In some embodiments, the growth media is selected from an effluent source, a modified effluent source, groundwater, contaminated groundwater, wastewater, sewage, landfill leachate, sugar refinery waste, paper pulping waste, bakery waste, brewery waste, and fluid compositions comprising bacterial factors, or any combination thereof. In illustrative embodiments, the electrogenic bacteria comprise mixed culture bacteria, *Rhodoferax* sp. bacteria, or *Geobacter* sp. bacteria, or any combination thereof. In some embodiments, the electrogenic bacteria are selected from the group consisting of *G. sulfurreducens* and *R. ferrireducens*, or any combination thereof. Embodiments also include culturing, batch culturing, semi-batch culturing, or continuous culturing, and combinations thereof.

The steps of the present methods are computer automated in various embodiments. In some embodiments, the harvesting entails separating the biolayer from the substrate, where the separating is mechanical, chemical, biological, or electrical, or any combination thereof. In some embodiments, the mechanical separation is by shearing. In other embodiments, the shearing is fluid shearing, pressurized shearing, sonication, or by shaking, or any combination thereof. In some embodiments, the bacteria, the biolayer and/or the biofilm, or any combination thereof, are subjected to filtration, centrifugation, chemical processing, electrophoresis, or cell disruption, or any combination thereof. In some embodiments, the foregoing steps permit industrial application of the biofilm.

In one aspect, the present invention provides an apparatus, including (a) a compartment configured to receive an influent source, (b) a bioelectrochemical cell having one or more of an electroactive biofilm and one or more tubular modules contained within the compartment, where the one or more tubular modules comprise one or more of at least one electrode, one or more mesh separators, one or more membranes, and a gas diffusion layer, and (c) one or more platforms configured to engage the one or more tubular modules. In some embodiments, the apparatus is a reactor, where the reactor is an energy-reactor or a cell-reactor. In some embodiments, the reactor is an energy-reactor comprises while in other embodiments the reactor is a cell-reactor. The apparatus of the present invention further includes an aeration basin in suitable embodiments.

The aeration basin encloses a plurality of the platforms engaging a plurality of the tubular modules in various embodiments. In some embodiments, the compartment contains the bioelectrochemical cell and the bioelectrochemical cell is a single bioelectrochemical cell. In other embodiments, the compartment contains the bioelectrochemical cell and the bioelectrochemical cell is a plurality of bioelectrochemical cells. In illustrative embodiments, the at least one electrode comprises an anode connected to an electrical circuit and a cathode connected to the electrical circuit. In some embodiments, the one or more mesh separators comprise materials selected from carbon mesh, pre-catalyzed carbon mesh, carbon paper, carbon felt, carbon powder, carbon foam, carbon cloth, graphite felt, nitrogen doped carbon, and corrosion resistant metals, or any combination thereof.

The corrosion resistant metals are selected from stainless steel, titanium, copper, silver, zinc, magnesium, iron, gold, aluminum, aluminum nitride, aluminum oxide, brass, cobalt, graphite, and beryllium, or any combination thereof in various embodiments. In some embodiments, the membrane is a proton exchange membrane. In some embodiments, the gas diffusion layer is a coated layer or an independently affixed layer in contact with the at least one electrode. In suitable embodiments, the gas diffusion layer is hydrophobic and oxygen permeable. In some embodiments, the gas diffusion layer is an elastomeric polymer selected from polydimethylsiloxane (PDMS) or polytetrafluoroethylene (PTFE), or both.

The apparatus of the present invention provides for one or more tubular modules positioned throughout the platform in angled, straight, slanted, tapered, polygonal, rectangular, square, circular, curved, diagonal, random, concentric, patterned, perimetric, polygonal, diamond, hexagonal, or triangular configurations, or any combination thereof in illustrative embodiments. In some embodiments, the components permit industrial application of the apparatus. In some embodiments, the bioelectrochemical cell is capable of producing an electrical current in the presence of the biofilm. The biofilm is capable of degrading organic constituents from the influent source in various embodiments. The influent source, in suitable embodiments, contains biomass from an effluent source, a modified effluent source, groundwater, contaminated groundwater, wastewater, sewage, landfill leachate, sugar refinery waste, paper pulping waste, bakery waste, brewery waste, and fluid compositions comprising bacterial factors, or any combination thereof. In some embodiments, the apparatus is a microbial fuel cell, a component of a microbial fuel cell, or configured for application to a microbial fuel cell or microbial fuel cell system.

In one aspect, the present invention provide for a system of producing an electroactive biofilm, including (a) a first solution containing electrogenic bacteria, (b) a first substrate for adherence of the electrogenic bacteria and biolayer formation, a second solution for receiving the biolayer, (d) a second substrate for adherence of the biolayer and formation of the biofilm, (e) a bioelectrochemical complex in fluid communication with the second substrate, and (f) an influent source. In some embodiments, the first solution or the second solution, or both, possess conditioning factors selected from mediators, $CaCl_2$, sulfur, cell growth media, cell proliferation factors, adherence factors, cell viability factors, cell density factors, and cell confluence factors, or any combination thereof in certain embodiments.

In some embodiments, the mediators are quorum-sensing inducers selected from the group consisting of N-Acyl Homoserine Lactones (AHL) and AI-2 autoinducers, or both. In some embodiments, the system includes a preservation housing, wherein the housing provides for storage of the biolayer or the biofilm, or both. In some embodiments, the housing further comprises liquid nitrogen, glycerol, glycerine, preservation chemicals, or any combination thereof. In certain embodiments, the housing is a desiccator. In some embodiments, the system further includes an automated monitoring device for monitoring one or more of pH, oxygen concentration, carbon dioxide levels, nitrogen levels, salinity, bacterial density, colony confluence, or voltage potential, or any combination thereof.

In illustrative embodiments, the automated monitoring device is a computer, and wherein the automation is accessible through a remote interface. In some embodiments, the system further includes a cell-stimulator for stimulating one or more of the electrogenic bacteria, the biolayer, and the biofilm. In some embodiments, the stimulating is selected from the group consisting of photostimulation, solar, concentrated wavelengths, radiation, nuclear radiation, and ionizing radiation, or any combination thereof. In some embodiments, the first solution, the second solution, or both, contain bacterial growth media, an effluent source, a modified effluent source, groundwater, contaminated groundwater, wastewater, sewage, landfill leachate, sugar refinery waste, paper pulping waste, bakery waste, brewery waste, and fluid compositions comprising bacterial factors, or any combination thereof.

The electrogenic bacteria of the present systems include mixed culture bacteria, *Rhodoferax* sp. bacteria, or *Geobacter* sp. bacteria, or any combination thereof in suitable embodiments. In some embodiments, the electrogenic bacteria are selected from the group consisting of *G. sulfurreducens* and *R. ferrireducens*, or any combination thereof. In some embodiments, first substrate is an electrode connected to an electrical circuit, while the electrode is an anode connected to the electrical circuit in illustrative embodiments. In some embodiments, the second substrate is an electrode connected to an electrical circuit. The electrode is an anode connected to the electrical circuit in various embodiments.

In illustrative embodiments, the electrode is composed of materials selected from carbon mesh, carbon paper, carbon felt, carbon powder, carbon foam, carbon cloth, graphite felt, nitrogen doped carbon, and corrosion resistant metals, or any combination thereof. In some embodiments, the corrosion resistant metals are selected from stainless steel, titanium, copper, silver, zinc, magnesium, iron, gold, aluminum, aluminum nitride, aluminum oxide, brass, cobalt, graphite, and beryllium, or any combination thereof. In some embodiments, the system is an industrial scale microbial fuel cell system.

In some embodiments, the bioelectrochemical complex is capable of producing an electrical current in the presence of the biofilm. The biofilm is capable of degrading organic constituents in suitable embodiments. In some embodiments, the bioelectrochemical complex is a microbial fuel cell. In illustrative embodiments, the influent contains biomass from an effluent source, a modified effluent source, groundwater, contaminated groundwater, wastewater, sewage, landfill leachate, sugar refinery waste, paper pulping waste, bakery waste, brewery waste, and fluid compositions comprising bacterial factors, or any combination thereof. In suitable embodiments, the at least one electrode includes multiple electrodes such that there are an equal number of anodes and cathodes. The equal number of anodes and cathodes operate at one or more potentials in some embodiments provided that the anodes or anode and the cathodes or cathode operate at one or more fixed ratio potentials.

BRIEF DESCRIPTION OF THE FIGURES

FIG. 1 is a schematic diagram showing an illustrative embodiment of a reactor of the present invention. FIG. 1A is a diagram of one tubular module of the present invention, while

FIG. 2 is a flow chart demonstrating the process of generating electricity from a microbial fuel cell while simultaneously treating wastewater.

DETAILED DESCRIPTION

Figure 1A:
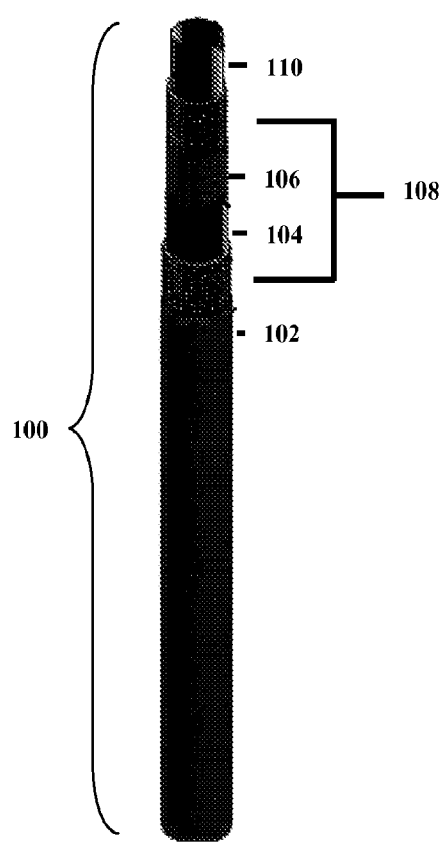
Figure 1B:
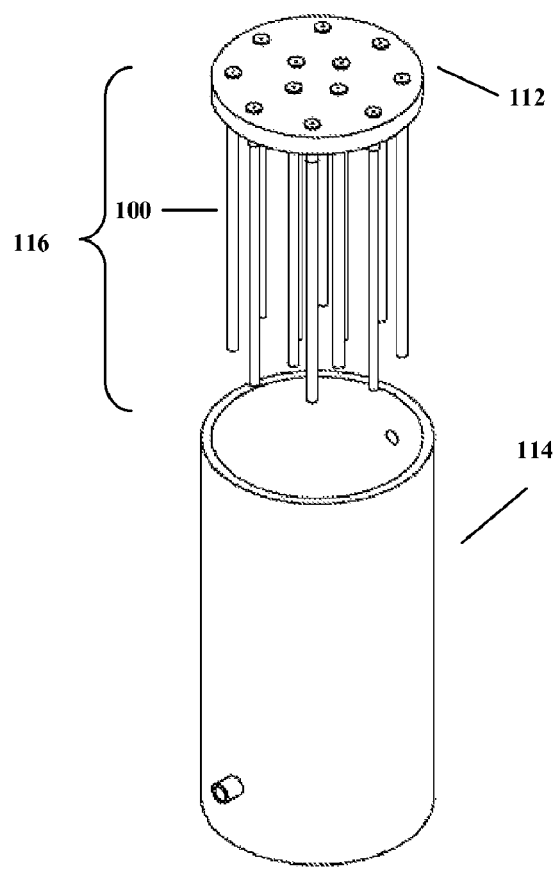
FIG. 1B shows a compartment configured to receive a plurality of tubular modules engaged with a platform.
Figure 1C:
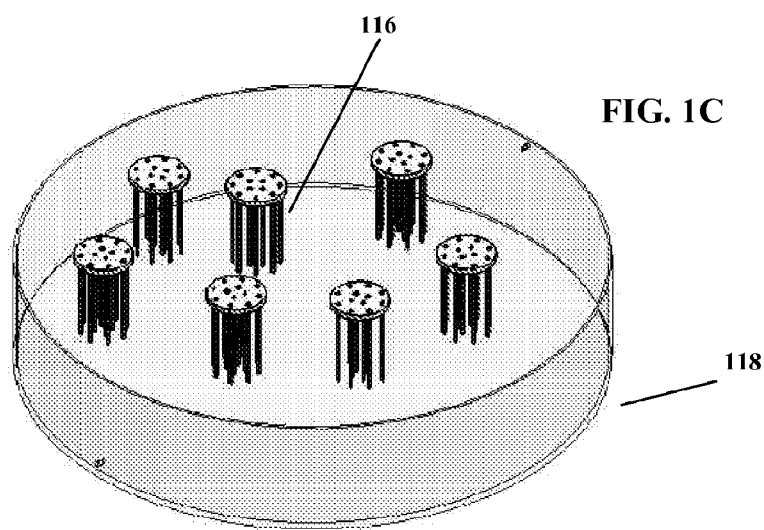
FIG. 1C further includes an aeration basin for receiving a plurality of tubular modules engaged with a platform.
Figure 1D:
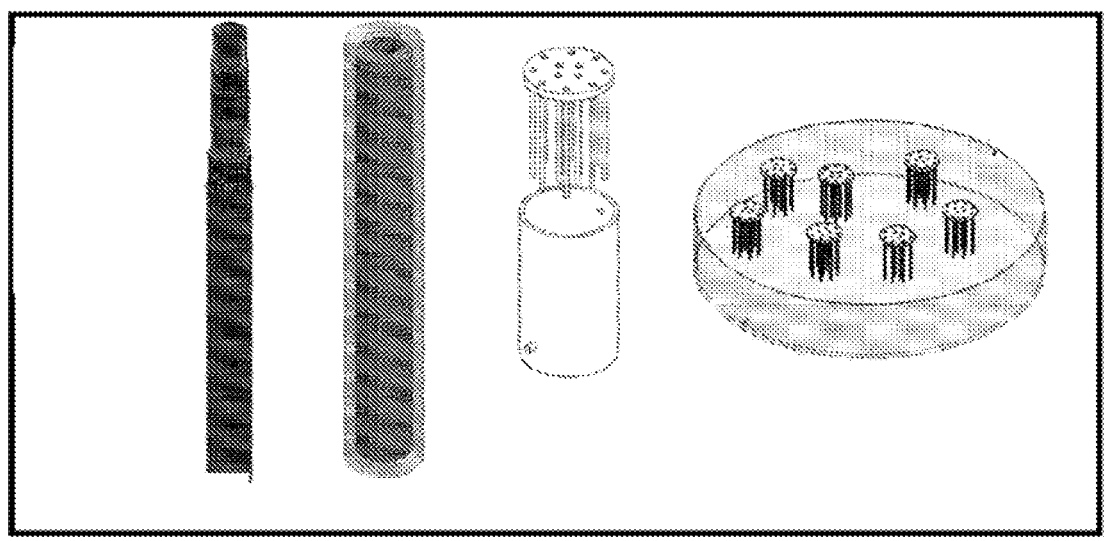
FIG. 1D shows a parallel representation of the components provided in FIGS. 1A-C.

In the following detailed description, reference may be made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made without departing from the spirit or scope of the subject matter presented herein.

As used herein, unless otherwise stated, the singular forms "a," "an," and "the" include plural reference. Thus, for example, a reference to "a bacteria" includes one or more bacterial cells. Also as used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein, the terms "aerobic" or "aerobic conditions" refer to conditions in a compartment or compartments that contain an amount of oxygen. Aerobic conditions may refer to one or more microbial environments during an oxidation reaction.

As used herein, the terms "anaerobic" or "anaerobic conditions" refer to conditions where oxygen is absent. Typically, anaerobic conditions refer to an environment where only anaerobic microorganisms can survive. Anaerobic conditions may refer to particular environments during an oxidation reaction.

As used herein, the terms "bioconductive" or "bioconductance," when referring to a biolayer and/or biofilm, denote the ability of a biological organism, e.g., microbes, bacterial cultures, biolayer and/or biofilm to facilitate the passage of an electric current through a conductor. In accord with the embodiments provided herein, the bioconductance of an microbial organism is directly related to the electric potential or voltage generated in a particular method, system, or from an apparatus. Bioconductance may also be measured with respect to an organism's capacity for generating power.

As used herein, the terms "biofilm" or "biofilms" refer to an aggregate of living cells which are connected and/or immobilized onto a surface as microbial colonies. The cells are typically embedded within a self-secreted matrix of extracellular polymeric substance (EPS), which is a polymeric mixture of nucleic acids, proteins and polysaccharides. Biofilms may form on living, non-living, organic, or inorganic substrates, and constitute a prevalent mode of microbial life in natural, industrial, and hospital settings. Biofilms can be cells of a unicellular microorganism, i.e., prokaryotes, archaea, bacteria, eukaryotes, protists, fungi, algae, *euglena*, protozoan, dinoflagellates, apicomplexa, trypanosomes, amoebae, and the like. "Electroactive biofilms" as used herein, refer to biofilms possessing specific electroactive properties, i.e., electron generating and/or bioconductance.

As used herein, the terms "biolayer" or "biolayers" refer to an aggregate of living cells which are connected and/or immobilized onto a surface as microbial colonies. The cells may be embedded within a self-secreted matrix of extracellular polymeric substance (EPS), which is a polymeric sticky mixture of nucleic acids, proteins and polysaccharides. Biolayers may form on living, non-living, organic, or inorganic substrates. Biolayers are precursors to biofilms inasmuch as a biolayer is formed prior to a biofilm, but is not necessary for biofilm formation. For example, when two substrates, e.g., two anodes, are employed for the generation of an electroactive biofilm, the culture formed on or adhered to the first substrate (prior to transfer to the second substrate) is the biolayer. While biolayers serve as precursors to biofilm formation, biofilms are not biolayer precursors. Biolayers, moreover, can be of a unicellular origin, e.g., prokaryotes, archaea, bacteria, eukaryotes, protists, fungi, algae, *euglena*, protozoan, dinoflagellates, apicomplexa, trypanosomes, amoebae, and the like.

As used herein, the terms "biomass", "biomasses", and/or "biomassive" refer to organic and/or inorganic compounds or materials that contain a source of energy for bacteria, e.g., electrogenic bacteria. Biomass and biomass constituents can be found in, but are not limited to, groundwater, contaminated groundwater, wastewater, sewage, landfill leachate, sugar refinery waste, paper pulping waste, bakery waste, brewery waste, fluid compositions containing bacterial factors, organic matter, wood or wood waste, straw, herbaceous crops, corn stover, grass such as switch grass, or other sources of annual or perennial grass, paper or paper waste, pulp and paper mill waste, municipal and/or industrial solid wastes, and the like.

As used herein, the terms "compartment" or "compartments" refer to devices or chambers that support a biologically active environment, typically a chamber capable of treating wastewater and/or allowing for biomass degradation via microorganism metabolism. A compartment may have various environmental conditions, such as, but not limited to, gas content, e.g., air, oxygen (or lack of oxygen), nitrogen (or lack of nitrogen), carbon dioxide, flow rates, temperature, pH, humidity, intensity of light, dissolved oxygen levels, and agitation speed/circulation rate. Compartments can be of any size, shape, or material, and of any configuration that will physically maintain an effluent source capable of providing for the generation of electricity. Acrylic compartments, for example, are suitable for smaller, laboratory scale embodiments, while compartments made of steel may also be used in large-scale production. See. e.g., Strasser, et al., *Lattice*-strain *control of the activity in dealloyed core-shell fuel cell catalysts. Nature Chemistry*, Vol. 2 pp. 454-460 (2010).

As used herein, the term "effluent" refers to any wastewater, waste, water effluent, or exhaust, and the like, that results from one or more processes and/or chemical reactions that is emitted by, e.g., flows from, a structure. The term "effluent" may be used interchangeably with the terms "wastewater", "waste," and "exhaust," etc. Likewise, "influent," as used herein, may be used interchangeable with effluent inasmuch as an effluent source is coterminous with the "influent" of a MFC. More generally, the terms "source," "fuel source," or "energy source," as used herein, refer to effluents and/or influents. The source may be in any suitable form, for example, gaseous effluent, liquid effluent, solid, e.g., particulate source, and/or any combination thereof. Sources of the present invention generally contain biomass and function as an influent to a MFC or MFC system, apparatus, etc.

As used herein, the term "electrogenic bacteria" refers to organisms that breakdown organic matter and transfer electrons to the surrounding environment, i.e., an anode, rather than an electron acceptor such as oxygen. Such electrogenic bacteria are capable of completely oxidizing organic compounds to carbon dioxide or other byproducts and then transfer the electrons derived from the oxidation onto the anode of a MFC. For example, electrogenic bacteria include organisms in the family Geobacteraceae including organisms from any of the *Geobacter, Desulfuromonas, Desulfuromusa, Pelobacter* or *Malonomonas* genera that are capable of oxidizing organic fuel compounds completely to carbon dioxide and/or are capable of dissimilatory Fe(III) reduction.

As used herein, the term "electrode" refers to an anode or a cathode. The "anode" is an electrode that facilitates the oxidation, i.e., the loss of electrons, of various biomass constituents. For example, the effluent may contains one or more saccharides which are oxidized by bacteria, i.e., electrogenic bacteria, at the anode. The "cathode" is an electrode that facilitates the reduction, i.e., gaining of electrons, of an oxidant, typically oxygen.

As used herein, the terms "immobilizing" or "immobilized" refer to the ability to retain a microbe, bacteria, biolayer and/or biofilm or any combination thereof, in or on a matrix, surface, particle, electrode, anode, cathode, or bead containing matrix. In some embodiments, methods for bacterial immobilizing encompass adherence to a matrix, surface, particle, electrode or bead containing matrix. Immobilization also includes adsorption, covalent binding, entrapment, membrane confinement, and cross-linking.

As used herein, the terms "treatment", "treating", or "treated" refer to the degradation of organic compounds within an effluent source, such as, e.g., wastewater. As disclosed herein, wastewater treatment requires the removal or degradation of organic material, i.e., biomass, to yield end products including treated wastewater and sludge. An effluent may be treated pursuant to filtering and/or degradation of organic material. An effluent may be further "treated" in the presence of bacteria capable of breaking down organic constituents within the effluent.

Overview

The present invention relates generally to methods, systems, devices and device components of microbial fuel cells (MFCs) and other bio-electrochemical systems (BES) for the generation of electricity and remediation, i.e., treatment, of contaminated sources, e.g., wastewater, among others. The source, such as wastewater, is provided as a continuously replenishable biomass that "feeds" the microbial component of a MFC. Microbes, such as, e.g., electrogenic bacteria, exploit organic impurities, pollutants and/or contaminants contained in the biomass by degrading the impurities to extract energy. Consequently, MFC microbes possess coterminous functions with respect to contaminant degradation or remediation of a biomass-source, i.e., influent, and generating electricity inasmuch as influent remediation imparts an electron source necessary for establishing an electrical current.

Current MFC technology, however, fails to effectively generate electricity at least to the extent that electron densities at the electrodes are typically sub-optimal, which therefore imparts poor electron transport. Insufficient electrode surface area can further decrease microbial growth, while the production of carbon dioxide further stymies efficient operation of present MFC technologies. Hence, rather than employing MFCs, current source treatment protocols degrade impurities via chemicals, by physical removal of unwanted particulates, or though microbial remediation in the absence of MFC technology, i.e., without producing electricity. Such methods are not only inefficient and costly, but can be deleterious to the environment. These techniques typically require the introduction of oxygen via aeration, which is an expensive process that increases precipitously on an industrial scale. Oxygen is nevertheless an essential component of microbial remediation at least insofar as it is required for aerobic bacterial respiration. Aerobic respiration is an integral process for many metabolic pathways of microbes because oxygen functions as the necessary final electron acceptor.

Previous attempts to remedy the foregoing obstacles have failed at least because economical MFC methods, systems, and devices concerning anode inoculation have not come to fruition. One reason for this emanates from the difficulties associated with growing and maintaining an electrogenic culture, which can take 3 months or longer. See, e.g., Logan "Essential Data and Techniques for Conducting Microbial Fuel Cell and other Types of Bioelectrochemical System Experiments." *Chem Sus Chem.* 2012; 5(6):988-94. Likewise, electrodes may not be fully colonized with the appropriate electrogenic microbes, in part, because unwanted non-electrogenic species, which may possess higher growth rates compared to electrogenic species, infiltrate MFC cultures and squelch electrogenic bacterial proliferation and therefore decreases MFC efficiency and output. Further still, a biomass energy source is required for electrogenic bacterial proliferation, which imparts yet another barrier to MFC implementation unless an appropriate source can be identified and harnessed.

The present invention creatively transcends the foregoing obstacles, in part, by employing a biomassive effluent source such as, e.g., groundwater, contaminated groundwater, wastewater, sewage, landfill leachate, sugar refinery waste, paper pulping waste, bakery waste, brewery waste, fluid compositions containing bacterial factors, organic matter, wood or wood waste, straw, herbaceous crops, corn stover, grass such as switch grass, or other sources of annual or perennial grass, paper or paper waste, pulp and paper mill waste, municipal and/or industrial solid wastes, and/or fluid compositions comprising bacterial factors, or any combination thereof. The biomass typically contains waste contaminants that are broken down into simple sugars and other bioconstituents to support electrogenic culture growth pursuant to the present invention. As such, in concert with the electrogenic cultures, the source-biomass provides a continuous supply of electrons for generating electricity while sustaining electrogenic bacterial culture growth and metabolism.

In particular, electrogenic bacteria present at an electrode exploit organic impurities present in an effluent source, e.g., wastewater, such as, without limitation, glucose, acetate, and other source constituents into carbon dioxide, protons and electrons. Under aerobic conditions, electrogenic bacteria use oxygen or nitrate as an electron acceptor, thereby producing water. However, when oxygen is absent at the anode, electrogenic bacteria are conditioned to switch from their natural electron acceptor, i.e., oxygen, to an insoluble acceptor, such as the electrode. In this respect, the anode-respiring electrogenic bacteria directly transfer electrons to an insoluble acceptor though a "bioconductive" process, I.e., electrogenic-mediated metabolism.

The bioconductive capacity of the bacterial cultures, and biolayers and biofilms generated therefrom, detailed herein, provide the bases for efficient MFC systems, methods, and devices capable of operating at an industrial scale. High capacity MFCs, however, cannot properly function without sufficient colonization of the appropriate bacteria at the anode. And the extended growth phase of some electrogenic cultures proscribe rapid proliferation and aggregate formation, e.g., establishing biolayers or biofilms, required for sustainable energy production and source remediation. The present invention resolves these impediments by providing MFC systems, devices and methods that, for example, favor electroactive bacterial growth over non-electrogenic species to generate electroactive biofilms, which are printed on an surface thereby forming a bioactive electrode that can be readily integrated into a variety of manufacturing processes, such as, e.g., wastewater treatment systems.

Methods

In one aspect, the present invention provides a method of producing an electroactive biofilm by culturing electrogenic bacteria to form a biolayer on a substrate, where the biolayer possess a bioconductance, harvesting the biolayer, and applying the biolayer to a surface to form the biofilm, where the biofilm possesses increased bioconductance compared to the bioconductance of the biolayer. In short, by harvesting the biolayer formed from the initial culture of electrogenic bacteria, and subsequently applying the biolayer to a surface, the methods of the present invention actively select for an electroactive biofilm possessing greater bioconductive properties compared to other MFC systems employing biocatalytic components in the absence of positive selection.

In illustrative embodiments, a variety of inoculant sources are employed for culturing. Such sources include, but are not limited to, e.g., groundwater, contaminated groundwater, wastewater, sewage, landfill leachate, sugar refinery waste, paper pulping waste, bakery waste, brewery waste, fluid compositions containing bacterial factors, organic matter, wood or wood waste, straw, herbaceous crops, corn stover, grass such as switch grass, or other sources of annual or perennial grass, paper or paper waste, pulp and paper mill waste, municipal and/or industrial solid wastes, and fluid compositions comprising bacterial factors. The bacterial factors, moreover, are selected from divalent metal cations, one or more metals, iron, manganese, sulfites, phosphorus, calcium, and one or more proteins, or any combination thereof in suitable embodiments.

The culturing is additionally performed in the presence of bacterial growth media in some embodiments of the present invention. Similarly, adding growth media, replenishing growth media, and/or growth culture homogenization, or any combination thereof, are steps performed in accordance with the present methods in certain embodiments. Growth media cultures are generally known in the art and include, but are not limited to, for example, LB Broths, M9 Broths, Terrific Broth, Super Broth, MacConkey's MAC, Mannitol Salt MSA, Blood Agar BAP, Tryptic Soy Agar TSY, Actinoplanes medium, Bennett's medium, *Bacillus* agar, *Bacillus* broth, Blue green algae agar, Blue green algae broth, CASO agar, *Corynebacterium* agar, *Gluconobacter* agar, LB Agar, LB broth, LB broth (low salt), M17 media, M9 minimal media, Mannitol agar, Mannitol broth Marine agar, Marine broth, Methylamine Salts Agar, Methylamine Salts Medium, Modified Chopped Meat Medium, MY medium, Maltose yeast extract bacterial growth medium, Nutrient agar, Nutrient broth, MRS media, N-Z amine agar with soluble starch and NZCYM, NZM, NZ amine, NaCL, and magnesium sulfate, NZYM Oatmeal agar, Phenol red lactose broth, Potato-Carrot Medium, PYS agar, SOB media, SOC media, Terrific broth, TSY agar, TSY broth, YMG agar, YMG, YPD Agar, YPD media, YPG media, YT (2×), and Minimum Essential Medium (MEM).

Bacterial cultures of the present invention are stimulated in suitable embodiments to increase growth, proliferation, electrode adherence, and to facilitate biolayer and/or biofilm formation. Likewise, some embodiments provide for biolayer and/or biofilm stimulation. The stimulating as provided herein occurs via photostimulation, solar stimulation, directing light source wavelengths to cultures, radiation-based stimulating including nuclear radiation and/or ionizing radiation stimulation, or any combination thereof in some embodiments. The present methods further provide for electrogenic bacterial batch culturing, semi-batch culturing, or continuous culturing, or any combination thereof.

Moreover, mixed bacterial cultures, i.e., containing mixed or different bacterial species, may be employed in illustrative embodiments for generating sufficient bacterial densities. A variety of electrogenic bacteria are known in the art and can used in accordance with the present methods. See, e.g., Torres et al., "Selecting anode-respiring bacteria based on anode potential: phylogenetic, electrochemical, and microscopic characterization." *Environ Sci Technol.* 2009; 43(24):9519-27. For example, *Rhodoferax* sp. or *Geobacter* sp. or both are the cultured bacteria in certain embodiments. In this respect, such electrogenic bacteria may be one or more bacterial species selected from *G. sulfurreducens* and *R. ferrireducens*, or both. The skilled artisan will readily appreciate that various other electrogenic bacterial species can be employed for the same purpose.

Culturing is performed and modified, as desired, for suitable applications requiring a particular density and/or confluence, which can be for about 1, 2, 3, 4, 5, 6, 7, 8, 9, 10, 11, 12, 13, 14, 15, 16, 17, 18, 19, 20, 25, 30, 35, 40, or 50 days. In illustrative embodiments, the bacteria are cultured for about 13, 14, 15, 16, 17, or 18 days. In other embodiments, the bacteria are cultured until a desired cell density is attained, while some embodiments provide for bacterial culturing until electrode confluence in achieved. The amount of time required for biolayer and/or biofilm formation depends upon a variety of factors, such as, e.g., cell health, media, electrode adherence, etc. The skilled artisan will readily appreciate that the cultures of the present invention can be optimized to achieve a particular end-point by altering culture conditions suitable for any particular need.

In accord, present methods include bacterial, biolayer, and/or biofilm conditioning in illustrative embodiments, where the conditioning improves bioconductivity compared to the bioconductivity in the absence of the conditioning. In suitable embodiments, the conditioning is selected from introducing electron shuttling mediators, cell-signaling mediators, CaCl, $CaCl_2$, sulfur, cell growth media, cell proliferation factors, adherence factors, cell viability factors, and/or increasing bacterial cell density or confluence, or any combination thereof. The conditioning may also include addition of ferric chloride, hemoglobin, amino acids, casamino acids, amino acids containing sulfur groups, trace metals, NTA, $MgSO_4$, $MnSO_4$, NaCl, $FeSO_4$, $CoCl_2$, $AlK(SO_4)_2$, $H_3BO_3$, $Na_2MoO_4$, $NiCl_2$, $Na_2WO_4$, and/or quorum sensing (QS) signaling molecules, or any combination thereof.

In this regard, bacterial QS, e.g., electrogenic bacterial QS, enables intra- or inter-species communication, which provides for stimulus response and, when induced, alteration of bacterial density at one or more locations. However, different bacterial species may employ various cell-signaling mediators, e.g., molecules, QS signaling molecules and/or inducers or autoinducers, for communication. Such mediators include, but are not limited to, N-Acyl Homoserine Lactones (AHL) in Gram-negative bacteria, and a family of autoinducers known as AI-2 in both Gram-negative and Gram-positive bacteria. As such, in illustrative embodiments of the present invention, the mediators are quorum-sensing inducers selected from N-Acyl Homoserine Lactones (AHL) and AI-2 autoinducers, or both.

Biofilm or biolayer formation to this end typically depends on QS signaling. In fact, genetic analyses have demonstrated extracellular signaling induces the production and/or modification of differentiated biolayers and/or biofilms. See, e.g., Li et al., "Factors Affecting Biofilm Formation in Mediatorless Microbial Fuel Cells." *Chem. Biochem. Engr.* 2010; 24:341-346. The present invention thus employs cell-signaling mediators, QS molecules, signaling molecules, inducers, and the like in certain embodiments to facilitate biolayer and/or biofilm formation. The basic components required for biofilm or biolayer formation, moreover, include microbes, a colonization surface, and a glycocalyx, i.e., a protective coating composed of exopolysaccharides and water. Biolayer and biofilm adherence—to surfaces and to each other—is facilitated through the production of pili and related adherence factors in suitable embodiments.

While QS mediators facilitate biolayer and/or biofilm formation, electron shuttling mediators, such as, but not limited to, for example, phenolic compounds, are not an essential component of the present methods. Such shuttling mediators can be expensive, toxic, and may decrease MFC efficiency and therefore should only be used when necessary. Nevertheless, due to the high conversion efficiency envisaged by the methods of the present invention, electron transfer readily occurs in the absence of electron shuttling mediators. To this end, some embodiments contemplate electrogenic bacterial, e.g., *G. sulfurreducens* and/or *R. ferrireducens* conversion, i.e., of electrons to electric current for at least about 20, 40, 60, or 80% of the produced electrons, while in other embodiments, conversion efficiency is contemplated from at least about 60 to 80% of the produced electrons to an electric current.

Methods of the present invention further include monitoring one or more culturing factors selected from, but not limited to, pH, oxygen concentration, carbon dioxide levels, nitrogen levels, salinity, bacterial density, colony confluence, and electrical potential, or any combination thereof. Electrical potential, i.e., voltage, is generated pursuant to an electron imbalance between an anode and a cathode, as more fully described below. The voltage is monitored according to various embodiments of the present invention and, if necessary, externally adjusted for maintaining continuous MFC operation.

In particular, illustrative embodiments of the present invention provide for an electrogenic bacterial culture, biolayer and/or biofilm-generated voltage between about from −50V to 50V, −10V to 10V, −5V to 5V, or about from −2V to 2V. In some embodiments, the voltage is between about from −5V to 5V, while in others it is about from −0.5V to 0.5V. These electric potentials are similar to those generated in a typical hydrogen fuel cell, and the skilled artisan will readily appreciate that higher voltages can be obtained by connecting multiple circuits in series.

According to the present methods, voltage monitoring or monitoring of any other culturing factor may be manual, I.e., employing individual or various electric and/or biologic assessments of culture parameters using methods known in the art, or automated by using a computer-assisted program and/or wireless device or transmitter. The skilled artisan will appreciate that a variety of technologies exist to facilitate culture monitoring and can be used in accordance with the present invention.

Moreover, in suitable embodiments, the present methods include regulating gas concentrations contained in one or more MFC compartments harboring the electrogenic bacterial cultures, biolayers, and/or biofilms. Specifically, gas regulating transpires pursuant to the application of an elastomeric polymer selected from polydimethylsiloxane (PDMS) or polytetrafluoroethylene (PTFE), or both. In some embodiments, the elastomeric polymer functions as a conduit for regulating oxygen and/or nitrogen. Control of such gaseous diffusion is achieved via advective flow. See, e.g., Cheng et al., "Increased Power Generation in a Continuous Flow MFC with Advective Flow through the Porous Anode and Reduced Electrode Spacing." Environ. Sci. Technol. 2006; 40(7):2426-2432.

Electrogenic bacterial culturing occurs in the present of a substrate, e.g., an electrode such as an anode or a cathode, as further detailed below. The resulting biolayer formed on the anode is subsequently harvested. Harvesting entails separating the biolayer from the anode, where, in certain embodiments, separating techniques include, but are not limited to, mechanical separating, chemical separating, biological separating, or electrical separating, or any combination thereof. In some embodiments, the separating is by shearing selected from fluid shearing, pressurized shearing, sonication, and shaking, or any combination thereof. Fluid and/or mechanical shearers can be employed for such techniques and are well known in the art. Thereafter, the unbound biolayer is subjected to filtration, centrifugation, chemical processing, electrophoresis, and/or cell disruption, or any combination thereof in suitable embodiments. Likewise, such techniques may be employed to enhance any form of bacterial culture as provided herein, i.e., the electrogenic bacterial culture, biolayer and/or biofilm.

The harvested biolayer is then applied to a surface in illustrative embodiments of the present invention. The applying is selected from, but not limited to, cell-printing, piezoelectric printing, coated rolling, roll-to-roll conveying, spray nozzle application, electroactive deposition, magnetoactive deposition, laser induction, and biological laser printing, or any combination thereof. Suitable embodiments of the present invention employ cell-printing technology for biolayer-to-surface application. In this regard, a standard ink-jet printer is reconfigured to allow for cell printing on the surface (see U.S. Pat. Nos. 7,051,654 and 5,668,581 and U.S. Pat. Pub. No. 2010/0033545), which is selected from, but not limited to, an electrode surface, a catalyzed electrode surface, and catalytic materials enveloping an electrode surface or a catalyzed electrode surface. In illustrative embodiments, the surface is a nitrogen-doped carbon mesh.

Embodiments of the present invention include bacterial deposition using techniques, such as, e.g., piezoelectric ink-jet processes (see U.S. Pat. Nos. 7,051,654 and 5,668,581 and U.S. Pat. Pub. No. 2010/0033545), including single or multiplex configurations (see U.S. Pat. No. 6,997,550), liquid nozzle spray (see U.S. Pat. Pub. No. 2009/0087896), electroactive deposition processes (see U.S. Pat. Pub. No. 2002/0008746), magnetoactive deposition processes, laser-induced forward transfer processes (see Serra et al., "Laser-Induced Forward Transfer: A Laser-Based Technique for Biomolecules Printing." Cell and Organ Printing, 2010), biological laser printing utilizing nano-laser and femto-laser technologies (BioLP; see Ringeisen et al., "Biological Laser Printing (BioLP) for High Resolution Cell Deposition." Cell and Organ Printing, (2010), and/or PDMS stamp for microcontact printing).

In some embodiments, PDMS stamp microcontact printing is employed, where the stamp is prepared using an elastomeric polymer such as PDMS. Such a stamp is prepared, in illustrative embodiments, by pouring a mixture of an elastomer such as Sylgard® 184CA brand PDMS in a master, such as, e.g., a silicon master, with a curing agent in an appropriate curing ratio such as, e.g., a 10:1 ratio of PDMS to curing agent. The width and depth of the relief varies according to the application and any shape can be used to provide surfaces with various regions which contain the biolayer and/or biofilm. In one exemplary application, the width of the relief is 15 μm and the depth of the relief is about 20 μm.

After removal of entrained air bubbles such as by use of an applied vacuum, the mixture is allowed to cure. The stamp is then gently removed and rinsed. The rinsed stamp is then "inked" by placing a small drop of solution, e.g., containing the desired bacterial population on the stamp. The cells are incubated on the stamp for an appropriate period of time of about 5 seconds to about 15-20 minutes. Subsequently, the PDMS stamp is employed for depositing cells on one or more substrates such as electrodes. It will be readily apparent to the skilled artisan that there are a profusion of application modifications and various additional methods concerning the foregoing applications.

The import of bacterial cell application is manifest with respect to the present invention at least because such techniques can be employed for substrate and surface application. In various embodiments, the surface is composed of one or more materials selected from, but not limited to, carbon mesh, carbon paper, carbon felt, carbon powder, carbon foam, carbon cloth, graphite felt, nitrogen-doped carbon, and corrosion resistant metals in some embodiments. Such corrosion resistant metals are selected from, but not limited to, stainless steel, titanium, copper, silver, zinc, magnesium, iron, gold, aluminum, aluminum nitride, aluminum oxide, brass, cobalt, graphite, and beryllium, or any combination thereof. In certain embodiments of the present invention, the surface is the exterior surface of a second substrate, where the second substrate is an electrode such as an anode or a cathode. In some embodiments, the surface is a material substantially enveloping the second substrate.

Typically, the substrate electrode is an anode, but may be a cathode in various embodiments. Nevertheless, suitable embodiments provide a second substrate configured as a bioactive anode designed for use in one or more MFCs and/or transport to a MFC. Roll-to-roll conveyer processes elucidate efficacious means for transporting the bioactive anode, as described in, e.g., U.S. Pat. Pub. No. 2002/0183180. Prior to transport, however, the bioactive anode containing the biofilm is preserved in suitable embodiments. While preservation, if employed, typically occurs at this stage, the invention is not so limited, i.e., preservation of any bacterial culture, biolayer, and/or biofilm preparations is suitable. In some embodiments, the preservation is selected from, but not limited to, freezing, flash freezing in liquid nitrogen, slow freezing in the presence of glycerol, glycerine-base preservation, desiccation, and chemical preservation, or any combination thereof.

As discussed above, the electric potentials or voltages are monitored at any or all stages of the present methods. Because voltage is a function of bioconductance (of the biolayer or biofilm) as defined herein, biolayer bioconductance is typically less than the bioconductance of the biofilm in accordance with the methods provided herein. In brief, selecting for an electroactive biofilm by, e.g., harvesting, conditioning, and/or applying the biolayer to the surface, the biofilm is selected for optimal electrogenic bacterial density, electrode adherence, electrogenic potential, and the like, compared to the biofilm precursors, i.e., the biolayer. As such, suitable embodiments impart a biofilm possessing an increased bioconductive capacity compared to the biolayer, where the difference is measured in electrode, e.g., anode, power output in suitable embodiments.

The methods of the present invention accordingly contemplated at least from about 100, 200, 300, 400, 500, 600, 700, 800, 900 or 1000 $mW/m^2$ of power to from about 500, 600, 700, 800, 900, 1000, 1200, 1500, 2000, 5000 or 10000 $mW/m^2$ generated from a electroactive biofilm colonized on an electrode. In some embodiments, the methods of the present invention provide at least from about 400, 500 or 600 $mW/m^2$ of power to from about 500, 600 or 700 $mW/m^2$ generated from a electroactive biofilm colonized on an electrode. While in suitable embodiments, it is contemplated that the methods of the present invention provide at least from about 500 to 600 $mW/m^2$ of power generated from a electroactive biofilm colonized on an electrode. In illustrative embodiments, the electrode in an anode.

Such electrical power is generated when the second substrate, e.g., an anode, is in fluid communication with an electrochemical complex capable of generating an electric current in the presence of electrons. In illustrative embodiments, the methods of the present invention provide for an electrochemical complex that is a microbial fuel cell (MFC) capable of supporting industrial power requirements, while concomitantly treating the source, e.g., wastewater, as further described below. See Lovely, *The Scientist. Fuel Cells*, p. 46 (2006).

Systems

In one aspect, the present invention provides a system for producing an electroactive biofilm, which includes a first solution containing electrogenic bacteria, a first substrate for adherence of the electrogenic bacteria and biolayer formation, a second solution for receiving the biolayer, a second substrate for adherence of the biolayer and formation of the biofilm, a bioelectrochemical complex in fluid communication with the second substrate, and an influent source. In this regard, by providing the foregoing solutions and substrates for respectively facilitating biolayer and biofilm formation, the present systems function to generate electroactive biofilm through selectively reducing inert bacteria unable to survive, proliferate, and function in accordance with the present systems, when presented with multiple substrates and solutions of the present invention.

Consequently, efficient electron capture at an electrode, such as an anode, is ascribed to the present systems which provide for an electroactive biofilm capable of completely oxidizing organic compounds to carbon dioxide while also directly transferring the derived electrons to the first and/or second substrate. The present systems therefore provide functional components for the production, maintenance, and housing of an electroactive biofilm capable of degrading organic impurities from an influent source, such as, for example, wastewater, while also generating electricity.

The present systems further include a preservation housing, where the housing provides for storage of the biolayer or the biofilm, or both in suitable embodiments. The housing further contains liquid nitrogen, glycerol, glycerine, or preservation chemicals, or any combination thereof in certain embodiments. In other embodiments the housing is configured as a desiccator for dehydration and storage of the electrogenic bacterial cultures, biolayers, and/or biofilms described herein. The first and second solutions of the present invention, moreover, possess viability factors that afford electrogenic bacteria and/or mixed-cultures, i.e., containing mixed or different bacterial species, essential nutrients for growth and proliferation in illustrative embodiments. *Rhodoferax* sp. or *Geobacter* sp. or both are present in the solutions of the present systems in certain embodiments. In this respect, such electrogenic bacteria may be one or more bacterial species selected from *G. sulfurreducens* and *R. ferrireducens*, or both.

In conjunction with the bacterial cultures present in the first solution, various embodiments of the present invention provide for a first solution that further contains unfiltered or filtered influent selected from, e.g., groundwater, contaminated groundwater, wastewater, sewage, landfill leachate, sugar refinery waste, paper pulping waste, bakery waste, brewery waste, fluid compositions containing bacterial factors, organic matter, wood or wood waste, straw, herbaceous crops, corn stover, grass such as switch grass, or other sources of annual or perennial grass, paper or paper waste, pulp and paper mill waste, municipal and/or industrial solid wastes, and fluid compositions comprising bacterial factors. In some embodiments, the bacterial factors are selected from divalent metal cations, one or more metals, iron, manganese, sulfites, phosphorus, calcium, and one or more proteins, or any combination thereof in suitable embodiments. In some embodiments, the bacterial factors are present in the first and second solutions.

Embodiments of the systems provided herein also include first and/or second solutions that contain conditioning factors selected from electron shuttling mediators, cell-signaling mediators, CaCl, $CaCl_2$, sulfur, cell growth media, cell proliferation factors, adherence factors, cell viability factors, and/or increasing bacterial cell density or confluence, or any combination thereof. The conditioning factors may also include ferric chloride, hemoglobin, amino acids, casamino acids, amino acids containing sulfur groups, trace metals, NTA, $MgSO_4$, $MnSO_4$, NaCl, $FeSO_4$, $CoCl_2$, $AlK(SO_4)_2$, $H_3BO_3$, $Na_2MoO_4$, $NiCl_2$, $Na_2WO_4$, and/or quorum sensing (QS) signaling molecules, or any combination thereof.

The first and/or second solutions further include, in illustrative embodiments, bacterial growth media. Likewise, the addition of growth media, replenishing growth media, and/or growth homogenization of bacterial cultures in the first and/or second solution are practiced in accordance with certain embodiments of the present invention. Growth media for culturing bacterial and/or electrogenic bacteria are known in the art and described above.

The solutions of the present invention are stimulated in suitable embodiments to increase growth, proliferation, electrode adherence, and to facilitate biolayer and/or biofilm formation. Likewise, some embodiments provide for stimulation of the bacteria present in the first solution to drive biolayer formation on the first substrate, while stimulation of the biolayer present in the second solution facilitates the establishment and adherence of an electroactive biofilm on the second substrate, respectively. Such stimulation is provided via a cell-stimulators selected from photostimulators, photoreactors, irradiators, polarizers, lasers, scanners, light emitting diodes (LED), s-NSOM, plasmonic waveguides, X-ray capacitors and/or machines, actuators, semi-conductors, solar stimulation devices, lenses, Sys*Stim® 206 muscle stimulator (model ME206, Mettler Electronics Corp., Anaheim, Calif.), Omnistim® 500 ES device (model 100500, International Academy of Physiotherapeutics, Inc., Topeka, Kans.), or Forte® ES device (model 074122, Chattanooga Group, Inc., Hixson, Tenn.), or any combination thereof in illustrative embodiments.

Such cell-stimulators may additionally include light sources, such as a laser, as well as optics and filters to present optimal light source wavelengths. The optics can be fiber optics for increased compactness. The system further includes one or more of an inverted and/or phase contrast microscope, CCD camera, compact fiber-based spectrometers, computer, software, and a flow collection system for monitoring and operating the present systems in suitable embodiments. The computer and the software may be automated to operate, record data, perform analyses, and/or compare the results to a database.

The first and second solutions detailed above function in concert with the cognate substrates of the present invention, i.e., the first solution is provided to a first substrate for biolayer formation and the second solution is provided to the second substrate for generation of the electroactive biofilm in illustrative embodiments. In this respect, the substrates of the present invention are selected from, but not limited to, an electrode, a catalyzed electrode, catalytic materials enveloping an electrode or a catalyzed electrode. While the first and second substrates may be identical, the present systems are not so limited. In this regard, either the first or the second substrate are composed of one or more, or any combination, of the foregoing substrates. In illustrative embodiments, the first and second substrates are nitrogen-doped carbon mesh surfaces enveloping an electrode such as an anode or a cathode.

In accord, the electrode and/or materials enveloping the electrode are composed of one or more materials selected from, but not limited to, carbon mesh, carbon paper, carbon felt, carbon powder, carbon foam, carbon cloth, graphite felt, nitrogen-doped carbon, and corrosion resistant metals in some embodiments. Such corrosion resistant metals are selected from stainless steel, titanium, copper, silver, zinc, magnesium, iron, gold, aluminum, aluminum nitride, aluminum oxide, brass, cobalt, graphite, and beryllium, or any combination thereof in certain embodiments of the present invention.

Typically, the electrode is an anode, but may be a cathode in various embodiments. Nevertheless, suitable embodiments provide a bioactive anode as the second substrate, which is configured for use in an electrochemical complex in fluid communication therewith. In some embodiments, the electrochemical complex is one or more MFCs or BESs. Application of the electrogenic bacterial culture to the first substrate for biolayer formation and/or the application of the biolayer to the second substrate, i.e., for electroactive biofilm formation, is selected from techniques including, but not limited to, cell-printing, piezoelectric printing, coated rolling, roll-to-roll conveying, spray nozzle application, electroactive deposition, magnetoactive deposition, laser induction, and biological laser printing, or any combination thereof. Suitable embodiments of the present invention employ one or more cell-printing technologies for biolayer-to-surface application. In some embodiments, a standard ink-jet printer is reconfigured to allow for cell printing. Other embodiments are described above and various applications will be readily appreciated by the skilled artisan. For example, in addition to a reconfigured ink-jet printer, as noted above, many dispensers and printing devices suitable for use are produce by Discovery Scientific (Vancouver, BC).

Different and additional components can also be incorporated into embodiments described above. For example, particular embodiments may include, but are not limited to, a computing system with one or more input interfaces, a communication interface, computer-readable medium, an output interface, a processor, a data processing application, a display, and a printer. Different and additional components may also be incorporated into the systems for a desired application, such as, e.g., computer-readable medium provides an electronic holding place or storage for information so that the information can be accessed by a processor as known to those skilled in the art. Computer-readable medium to this end may include, but is not limited to, any type of random access memory (RAM), any type of read only memory (ROM), any type of flash memory, etc. such as magnetic storage devices, e.g., hard disk, floppy disk, magnetic strips, etc., optical disks, e.g., CD, DVD, etc., smart cards, flash memory devices, etc. Such a computing system may have one or more computer-readable media that use the same or a different memory media technology.

Systems provided herein provide for efficient, high capacity treatment of effluent sources that function as a MFC influent as described above. Objectives regarding source treatment typically constitute the coagulation and removal of solid colloidal particles to stabilize organic biomass contained in the effluent. Specifically, particulate constituents, e.g., wastewater impurities, are oxidized and dissolved into end-products, e.g., $CO_2$, protons and electrons, while certain suspended colloidal solids may be incorporated into a biological floc, biolayer, and/or biofilm capable of exploiting carbonaceous organic matter.

Growth kinetics are measured in some embodiments to ascertain one or more of the following kinetic parameters: rate of soluble biomass utilization, rate of biomass growth, i.e., the rate at which the electrogenic bacteria proliferate as a function of how efficiently impurities are converted into cellular mass reduced by energy required for maintenance, rate of $O_2$ uptake, system/temperature effects, substrate-mass balance, $O_2$ required for sludge activation, as well as design and/or operating parameters, such as, e.g., food-to-microbe (F/M) ratio, which is defined as the rate of BOD or COD applied per unit volume of mixed liquor, and organic volumetric loading rate as defined by the amount of BOD or COD applied in an aeration tank volume per day.

Chemical oxygen demand (COD) and biochemical oxygen demand (BOD) are common parameters employed for indirectly measuring water-containing organic compounds, such as, but not limited to wastewater organic pollutants. COD is an indication of the mass of oxygen consumed per liter of solution, while BOD measures the amount of dissolved oxygen required by aerobic bacteria for degrading organic substrates constituents present in a wastewater sample, at a temperature, for a given time course. Both COD and BOD are typically measured in milligrams per liter (mg/L).

In this respect, certain embodiments of the present invention provide for normalized gCOD/l rates from about −0.001, −0.01, −0.1, −1, −5, and −10 to from about −0.01, −0.1, −1, −5, −10, −50, −100, and −500 gCOD/l. In suitable embodiments, normalized gCOD/l rates range from about −0.1, −1, −5, and −10 to from about −10, −50, and −100 gCOD/l. Other embodiments of the present invention provide for normalized $gCOD/m^2/hr$ rates from about −0.001, −0.01, −0.1, −1, −5, and −10 to from about −0.01, −0.1, −1, −5, −10, −50, −100, and −500 $gCOD/m^2/hr$. In suitable embodiments, normalized $gCOD/m^2/hr$ rates range from about −0.1, −1, −5, and −10 to from about −10, −50, and −100 $gCOD/m^2/hr$.

Such kinetic rates are optimized, moreover, when the reactors of the present invention (detailed below) are operated at certain electrode potentials (which are directly related to system resistance), that provides for minimal substrate consumption. In some embodiments, when the resistance is decreased, less substrate is consumed. In other embodiments, anaerobic bacterial metabolism provides for decreased substrate consumption when the resistance is increased, at least because increasing the resistance raises anode potential, which in turn drives efficient anaerobic metabolism. Accordingly, when a multi-electrode system is employed, a plurality of potentials can be used to optimize product formation and substrate consumption at one or more electrodes.

Furthermore, electrode complementation is important with respect to various embodiments of the present invention. Simply put, when resistance is high at an electrode, e.g., an anode, the resistance of the electrode should be sufficiently low enough to maximize efficiency. Likewise, when resistance is low at an electrode, e.g., an anode, the resistance of the electrode should be sufficiently high enough to maximize efficiency. The skilled artisan will readily appreciate that various resistance ratios and levels can be used for different outcomes. Because static electrode potentials tend to favor the growth of certain bacterial species, however, in order to maintain biodiversity the resistance ratios described above are reciprocated over various time intervals.

In certain embodiments, the present invention provides for an electrode potential and/or resistance, e.g., at the anode or cathode, from about 0.001, 0.01, 0.1, 1, 5, 10, 50, 75 and 100 to from about 0.1, 1, 5, 10, 50, 100, 125, 250, 500, 750 and 1000 ohms ($\Omega$). In some embodiments, the electrode potential and/or resistance, e.g., at the anode or cathode, is from about 10, 50, 75 and 100 to from about 50, 100, 125, 250 and 500$\Omega$. In suitable embodiments, the electrode potential and/or resistance, e.g., at the anode or cathode, is 125$\Omega$. In some embodiments, the potential and/or resistance, e.g., at the anode or cathode, is 10$\Omega$.

Apparatuses

In one aspect, the present invention provides an apparatus containing a compartment configured to receive an influent source, a bioelectrochemical cell ("BEC") having one or more of an electroactive biofilm and one or more tubular modules contained within the compartment, where the one or more tubular modules include one or more of at least one electrode, one or more mesh separators, one or more membranes, and a gas diffusion layer; and one or more platforms configured to engage the one or more tubular modules. FIG. 1. The compartment configured to receive the influent functions to facilitate the oxidation reaction occurring in the presence of the influent and the BEC. Specifically, the BEC serves as a conduit for assimilation of the electroactive biofilm with the influent to degrade influent contaminants while generating of electricity via bacterial metabolism.

In some embodiments, the apparatus contains a compartment that receives a continuous influent source. The influent may contain biomass which can be degraded or broken-down into components, such as, e.g., saccharide components, monosaccharides, and/or disaccharides, or other biological constituents. The saccharide components can then be used as an energy source for fermentation, electron transport, and/or electroactive biofilm metabolism by employing a bioelectrochemical cell as provided herein.

The influent is selected from an effluent source, a modified effluent source, groundwater, contaminated groundwater, wastewater, sewage, landfill leachate, sugar refinery waste, paper pulping waste, bakery waste, brewery waste, and fluid compositions comprising bacterial factors, organic matter, wood or wood waste, straw, herbaceous crops, corn stover, grass such as switch grass, or other sources of annual or perennial grass, paper or paper waste, pulp and paper mill waste, municipal and/or industrial solid wastes, and fluid compositions comprising bacterial factors, in illustrative embodiments. Moreover, the bacterial factors are selected from divalent metal cations, one or more metals, iron, manganese, sulfites, phosphorus, calcium, and one or more proteins, or any combination thereof in suitable embodiments. In some embodiments, for example, the influent is wastewater effluent which is treated in the compartment, while electricity is generated pursuant to the bioelectrochemical cell reactors of the present invention.

In particular embodiments, the one or more reactors of the present invention are selected from an energy-reactor and a cell-reactor. In some embodiments, the energy-reactor includes electrodes possessing large surfaces areas, as further described below, to maximize energy output, while also having small-diameter pore sizes as known in the art. In accord, the cell-reactor (cellular growth reactor) includes smooth electrode surfaces to allow for optimal harvesting. In some embodiments, the cell-reactor is coated with growth factors as described herein. Likewise mediators, chemical cathodes and/or growth factors are added to such reactors to encourage cell growth in suitable embodiments. Cell purity is optimized in various embodiments of the cell-reactors by increasing oxygen exclusion. Either or both of such reactors can be modified for optimal use by modifying or adding, e.g., various collectors, one or more layers of electrode materials, and the growth media.

Growth medias are known in the art and include, but are not limited to, for example, LB Broths, M9 Broths, Terrific Broth, Super Broth, MacConkey's MAC, Mannitol Salt MSA, Blood Agar BAP, Tryptic Soy Agar TSY, *Actinoplanes* medium, Bennett's medium, *Bacillus* agar, *Bacillus* broth, Blue green algae agar, Blue green algae broth, CASO agar, *Corynebacterium* agar, *Gluconobacter* agar, LB Agar, LB broth, LB broth (low salt), M17 media, M9 minimal media, Mannitol agar, Mannitol broth Marine agar, Marine broth, Methylamine Salts Agar, Methylamine Salts Medium, Modified Chopped Meat Medium, MY medium, Maltose yeast extract bacterial growth medium, Nutrient agar, Nutrient broth, MRS media, N-Z amine agar with soluble starch and NZCYM, NZM, NZ amine, NaCl, and magnesium sulfate, NZYM Oatmeal agar, Phenol red lactose broth, Potato-Carrot Medium, PYS agar, SOB media, SOC media, Terrific broth, TSY agar, TSY broth, YMG agar, YMG, YPD Agar, YPD media, YPG media, YT (2×), and Minimum Essential Medium (MEM).

The apparatus further includes an aeration basin for efficient biofilm production and operation in various embodiments. The aeration basin encloses a plurality of the platforms engaging a plurality of tubular modules in illustrative embodiments. In certain embodiments, the platforms and/or tubular modules are configured for transport and use in one or more industrial MFC systems. The present invention accordingly embodies a variety of apparatus applications that can be readily integrated into various manufacturing processes, such as, e.g., wastewater treatment systems. To this end, the multiplexed features of the present invention provide for high-throughput, industrial capacity applications, e.g., wastewater treatment.

Wastewater treatment reactors are nevertheless highly porous to avoid accumulation of particulate matter. Likewise, the tubular modules are configured to filter out particulate matter via one or more filters and/or mesh separators, as further detailed below. Such embodiments function in the presence or absence of water flow into the interior of the present apparatus. In conjunction with particulate filtration, electroactive biofilms present in the tubular modules, i.e., adhered to an electrode surface, must efficiently function to transfer electrons while maintaining stability. As such, certain embodiments impart an electroactive biofilm thickness optimized for stable and efficient transfer of electrons to at least one electrode, e.g., an anode, whereas the thickness of the electroactive biofilm may be, for example, between about 10-100 μm in some embodiments. Illustrative embodiments of the present invention provide for an electroactive biofilm thickness between about 50-80 μm.

Electron transfer efficiency is optimized in accordance with the foregoing by increasing the surface area of the electrodes in suitable embodiments. Such an increase in electrode surface area functions to increase power output in some embodiments. Without wishing to be limited by theory, it is contemplated that, for example, an approximate three- to five-fold increase in electric current can be obtained by increasing the surface area of the electrodes. For example, a surface area increase from about 0.0050 $m^2$ to about 0.030 $m^2$ can increase electric current by at least 10, 20, 30, 40, or 50% or more. It is contemplated that an increase in the surface area of the electrodes can also decrease wastewater retention times, which is important when employing a continuous effluent source. In some embodiments, at least from about 1, 5, 10, 25, 50, 100, 200, 300, 400, 500 or 1000 $cm^2$ of electrode surface area is envisaged. Illustrative embodiments provide for at least about 200 $cm^2$ of electrode surface area. The choice of electrode material may also affect power output.

Apparatuses of the present invention are contemplated to provide at least from about 100, 200, 300, 400, 500, 600, 700, 800, 900 or 1000 $mW/m^2$ of power to from about 500, 600, 700, 800, 900, 1000, 1200, 1500 or 2000 $mW/m^2$. In some embodiments, the apparatuses of the present invention provide at least from about 400, 500 or 600 $mW/m^2$ of power to from about 500, 600 or 700 $mW/m^2$. In some embodiments, it is contemplated that the apparatuses herein provide at least from about 500 to 600 $mW/m^2$ of power.

The power output emanates from a bioelectrochemical cell present in the compartment. In certain embodiments, the bioelectrochemical cell is a single bioelectrochemical cell, while in other embodiments, the bioelectrochemical cell is a plurality of bioelectrochemical cells. In either embodiment, including embodiments that are not explicitly denoted herein, the bioelectrochemical cell is capable of producing an electrical current in the presence of an electroactive biofilm and other components, such as, but not limited to, at least one electrode. The at least one electrode is at least one anode connected to an electrical circuit in some embodiments. In illustrative embodiments, the at least one electrode is at least one cathode connected to the electrical circuit.

Some embodiments of the present invention include a bioelectrochemical cell having one or more membranes. In various embodiments, the membrane provides for chemical exclusion as describe in Kim et al., "Power Generation Using Different Cation, Anion, and Ultrafiltration Membranes in Microbial Fuel Cells." *Environ. Sci. Technol.* 2007; 41(3):1004-1009. In illustrative embodiments, the membrane is an AMI-7001S anion exchange membrane, while other membranes include cation exchange membranes, i.e., a proton exchange membrane (PEM). A proton exchange membrane is a semi-permeable polymer typically made from ionomers, i.e., polymers composed of both electrically neutral units and ionized units. The PEM is capable of conducting protons while being impermeable to gases such as $O_2$ and H. Consequently, the function of a PEM, when incorporated into the present invention, is for proton transport while keeping the reactants separate.

Certain embodiments of the present invention provide tubular modules having an anode and a cathode. An air-cathode can be used for generating electricity from a non-aqueous system. The advantage of an air-cathode, i.e., compared to a cathode submerged in water, is that oxygen transfer to the cathode occurs directly from the air. Thus, because there is no requirement for oxygen to be dissolved in water, a quicker more efficient generation of electricity is possible. PEMs are nevertheless employed when generating electricity from an aqueous system in some embodiments. In other embodiments, the compartment containing the tubular modules operates under anaerobic conditions. To this end, electrogenic bacteria proliferate and oxidize organic matter, i.e., from the influent source, in the absence of oxygen. The oxidation reaction therefore produces electrons at the anode in the tubular module, which subsequently travel through an electrical circuit to the cathode. The migration occurs due to the charge difference created between the anode and the positively charge ions at the cathode. The electrical current is, thus, borne out of the charge difference.

Separating the anode and cathode are one or more mesh separators in some embodiments. The separators provide electrode support while concomitantly functioning to filter out unwanted particulates. Such separators of the present invention contain materials selected from carbon mesh, pre-catalyzed carbon mesh, carbon paper, carbon felt, carbon powder, carbon foam, carbon cloth, graphite felt, nitrogen doped carbon, or corrosion resistant metals, or any combination thereof in some embodiments. Such corrosion resistant metals are selected from stainless steel, titanium, copper, silver, zinc, magnesium, iron, gold, aluminum, aluminum nitride, aluminum oxide, brass, cobalt, graphite, and beryllium, or any combination thereof in certain embodiments of the present invention.

A gas diffusion layer is further provided within the one or more tubular modules in suitable embodiments of the present invention. This diffusion layer can be a coated layer or an independently affixed layer in contact with at least one of the electrodes. Illustrative embodiments further impart a hydrophobic, oxygen permeable gas diffusion layer composed of an elastomeric polymer selected from PDMS and/or PTFE, which is contained within the one or more tubular modules. A platform functions to connect the tubular modules, which are positioned throughout the platform in some embodiments. The module-platform positioning is selected from, but not limited to, angled, straight, slanted, tapered, polygonal, rectangular, square, circular, curved, diagonal, random, concentric, patterned, perimetric, polygonal, diamond, hexagonal, or triangular configurations, or any combination thereof.

The apparatuses of the present invention constitute MFCs, MFCs components configured for application to one or more different MFCs and/or MFC system in various embodiments. The MFC contains the electroactive biofilm capable of degrading organic constituents from an influent source, thereby producing carbon dioxide, protons, and electrons. Electrons are produced by an oxidation reaction and are concomitantly transferred to the anode by the electroactive biofilm. In certain embodiments, the electrons cannot pass through the PEM, and thus, are shunted through an electrical circuit, to the cathode. Protons simultaneously migrate through the PEM to the cathode. In some embodiments, an oxidant, such as oxygen, reacts with the protons and electrons at the cathode to form water. Accordingly, the electroactive biofilm can facilitate the generation of electricity in the presence of an influent source as detailed above.

FIG. 1 shows an illustrative embodiment of the present invention. Tubular module 100 is composed of anode 102, fine mesh 104, cathode 106, supporting mesh 108 and gas diffusion layer 110 operatively connected as shown in FIG. 1A. Platform 112 engages a plurality of tubular modules 100 forming a platform-tubular module complex 116, which provides increase electrode surface area for efficient electron transfer, as shown in FIG. 1B. Platform-tubular module complex 116 is housed within compartment 114 which provides for fluid communication between an influent source with platform-tubular module complex 116. Compartment 114 further includes an inflow channel through which the effluent is introduced. FIG. 1C illustrates aeration basin 118 containing a plurality of platform-tubular module complexes 116. FIG. 1D shows the components of the foregoing embodiment in parallel. Cathode 106 can be an air-cathode, and the one or more anodes 102 function as bioactive anodes having an electroactive biofilm adhered thereto. Air-cathode 106 and the one or more anodes 102 allow for efficient generation of electrons. The MFC further includes an external circuit connected to the MFC though electrical wires FIG. 2 shows a flow chart of an illustrative embodiment for effluent wastewater treatment and energy generation according to the methods of the present disclosure. In an operation 200, effluent such as but not limited to wastewater is received. In operation 202, electrogenic bacteria are cultured in the presence of wastewater effluent from operation 200, thereby forming a biolayer. In operation 204, the biolayer is harvested pursuant to conditioning factors of operation 206, such as bacterial growth media. Operation 208 provides for electrogenic culture purification from operation 202 and/or purification of the biolayer harvested from operation 204. Such purification techniques include, centrifugation, among other techniques known in the art.

Figure 3:
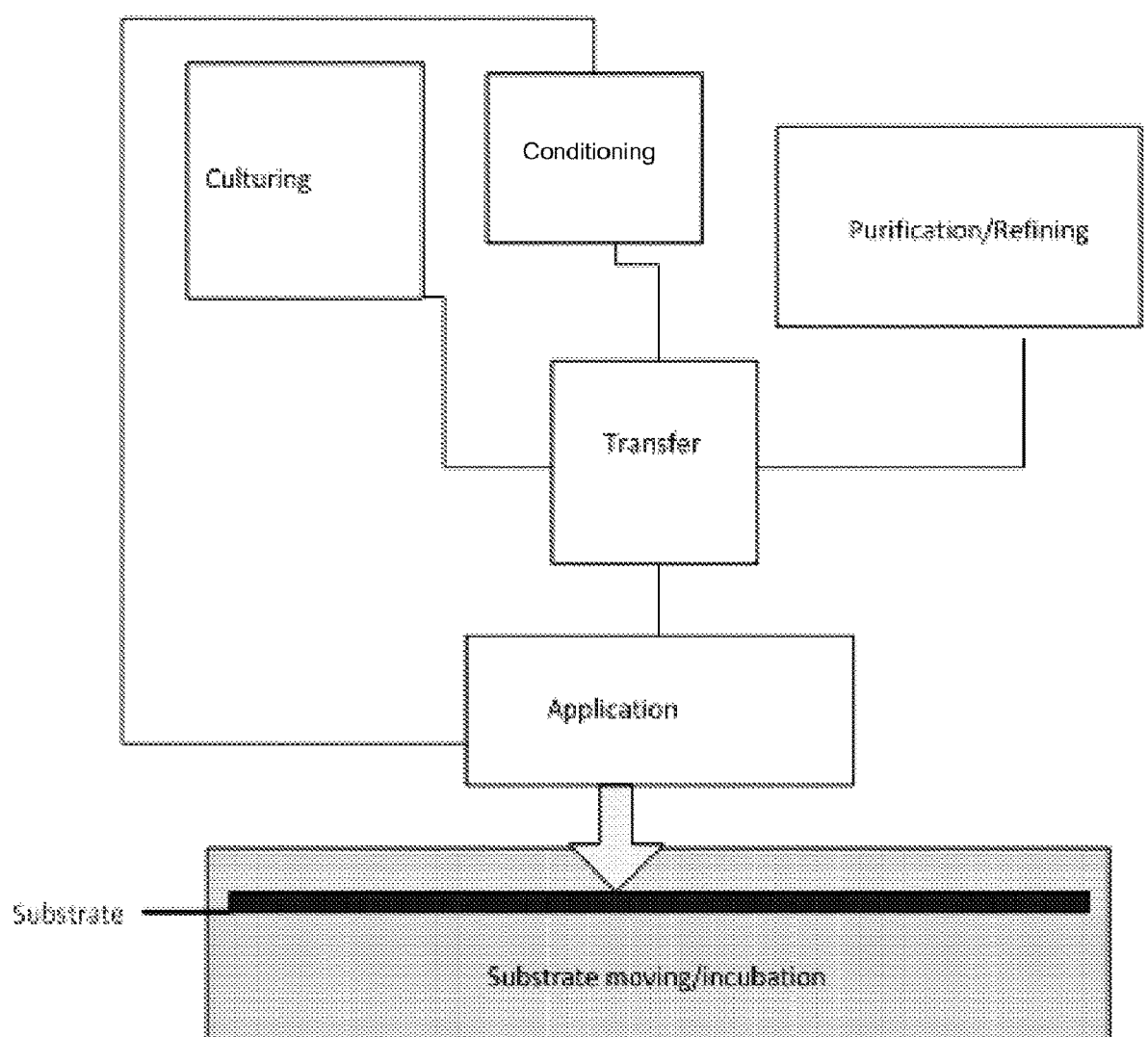
FIG. 3 is an alternative representation of a flow chart demonstrating the process of generating electricity from a microbial fuel cell while simultaneously treating wastewater.

In operation 210 the biolayer from operation 204 is applied to a new anode thereby selecting for an electroactive biofilm in accord with operation 212. Operation 214 indeed produces the electroactive biofilm thus establishing a bioactive anode, which is transferred to one or more MFC systems in operation 216. Electricity is generated in concert with remediation of the effluent from operation 200 as provided in operation 218. In operation 218, moreover, the generation of electricity occurs when an electric current is created by the migration of electrons through an electrical circuit from the foregoing operations. Electrons and hydrogen ions are produced as the electroactive biofilms metabolize the effluent. As the electrons travel through the wires, the hydrogen ions migrate to the cathode and subsequently form water when oxygen is present. FIG. 3 shows an alternative flow chart representation in accordance with the embodiments described above.

EXAMPLES

The present methods, systems and apparatuses will be understood more readily by reference to the following examples, which are provided by way of illustration and are not intended to be limiting in any way.

Example 1—MFC Reactor Efficiency

Empirical results were obtained with respect to reactor rates and normalized reactor rates of the present invention as measured via COD, gCOD/l, or $gCOD/m^2/hr$ and denoted below in Table 1 and as shown in FIGS. 4A-4G. In the figures, time is represented on the abscissa (x-parameter) and chemical oxygen demand parameters on the ordinate (y-parameter). The value for the normalized COD rate, as shown below in Table 1, is derived from the slope of the best linear fit derived from the x and y values.

TABLE 1

| Ref. No. | Time (hrs) | | Rate |
|---|---|---|---|
| | | Normalized gCOD/l | |
| 1.1 and FIG. 4A | 0 | 0.205 | −0.01116 |
| | 0.533333333 | 0.193 | |
| | 1.016666667 | 0.209 | |
| | 1.55 | 0.228 | |
| | 2.5 | 0.249 | |
| | 3.016666667 | 0.148 | |
| | 3.633333333 | 0.163 | |
| | 4 | 0.233 | |
| | 4.616666667 | 0.145 | |
| | 5.1 | 0.143 | |
| 1.2 and FIG. 4B | 0 | 0.205 | −0.01116 |
| | 0.533333333 | 0.193 | |
| | 1.016666667 | 0.209 | |
| | 1.55 | 0.228 | |
| | 2.5 | 0.249 | |
| | 3.016666667 | 0.148 | |
| | 3.633333333 | 0.163 | |
| | 4 | 0.233 | |
| | 4.616666667 | 0.145 | |
| | 5.1 | 0.143 | |
| | | COD | |
| 1.3 and FIG. 4C | 0 | 0.122 | −0.00481 |
| | 0.916666667 | 0.119 | |
| | 1.433333333 | 0.128 | |
| | 1.933333333 | 0.107 | |
| | 2.466666667 | 0.113 | |
| | 2.95 | 0.107 | |
| | 3.466666667 | 0.118 | |
| | 3.983333333 | 0.1 | |
| | 4.333333333 | 0.105 | |
| | 4.866666667 | 0.098 | |
| | 5.5 | 0.099 | |

| Ref. No. | Time (hrs) | COD | Rate | Normalize Rate $gCOD/m^2/hr$ |
|---|---|---|---|---|
| 2.1 and FIG. 4D | 0 | 76 | −1.65 | −0.03668 |
| | 1 | 77 | | |
| | 2 | 63 | | |
| | 3 | 57 | | |

TABLE 1-continued

Figure 4A:
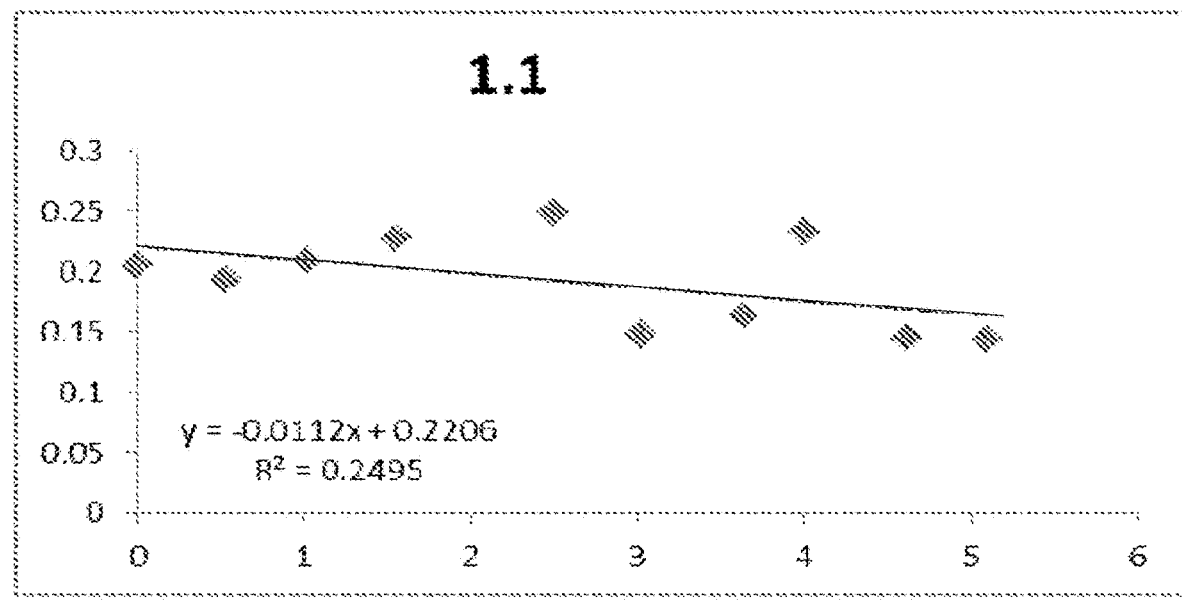
FIGS. 4A-G are graphs of representative experiments measuring reactor rates and normalizing the reactor rates as a function of time.
Figure 4B:
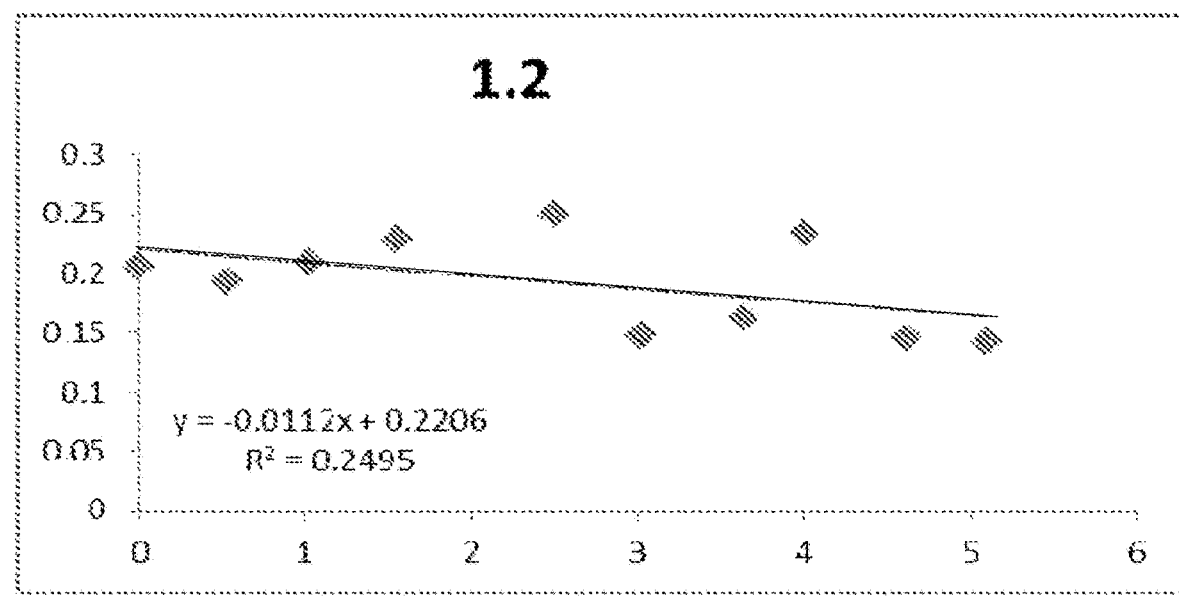
Figure 4C:
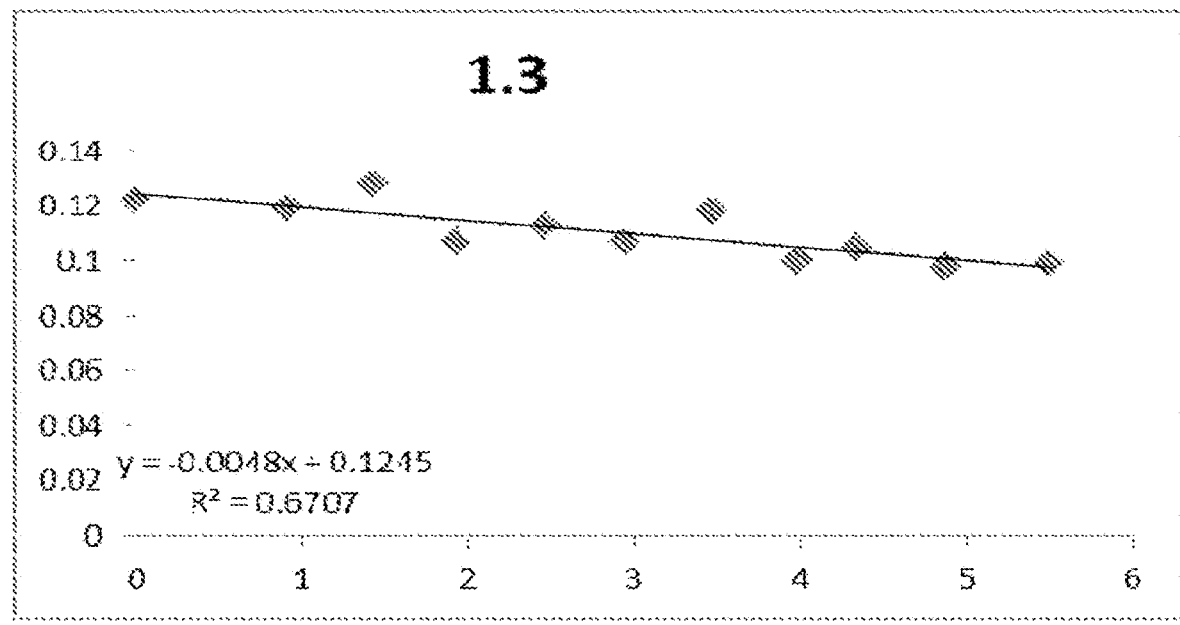
Figure 4D:
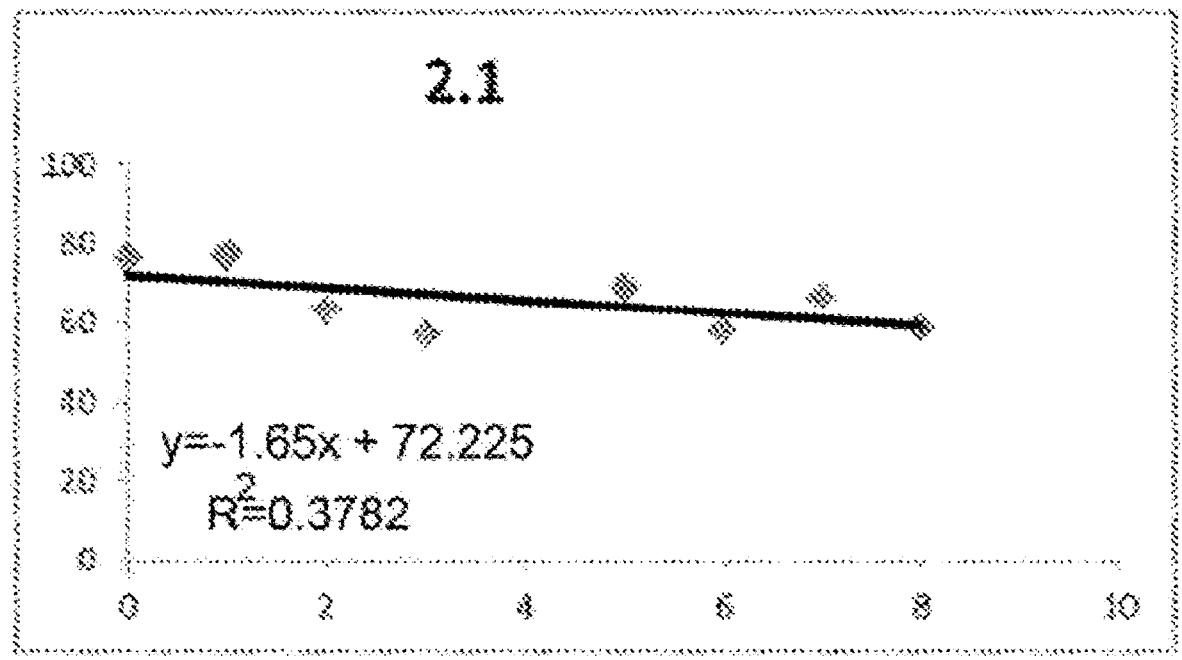
Figure 4E:
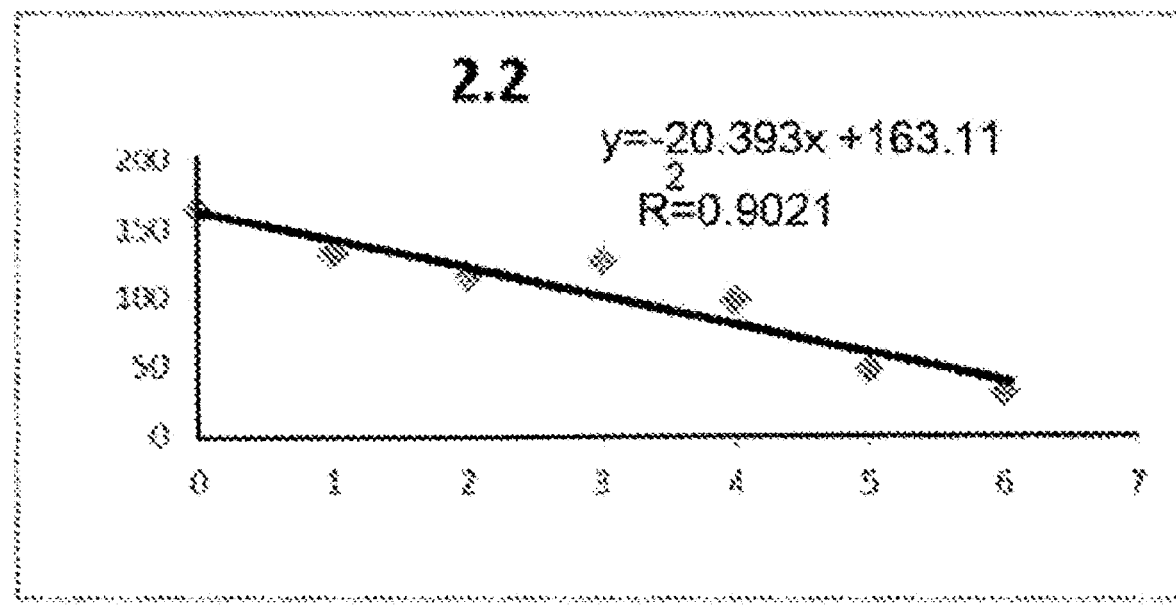
Figure 4F:
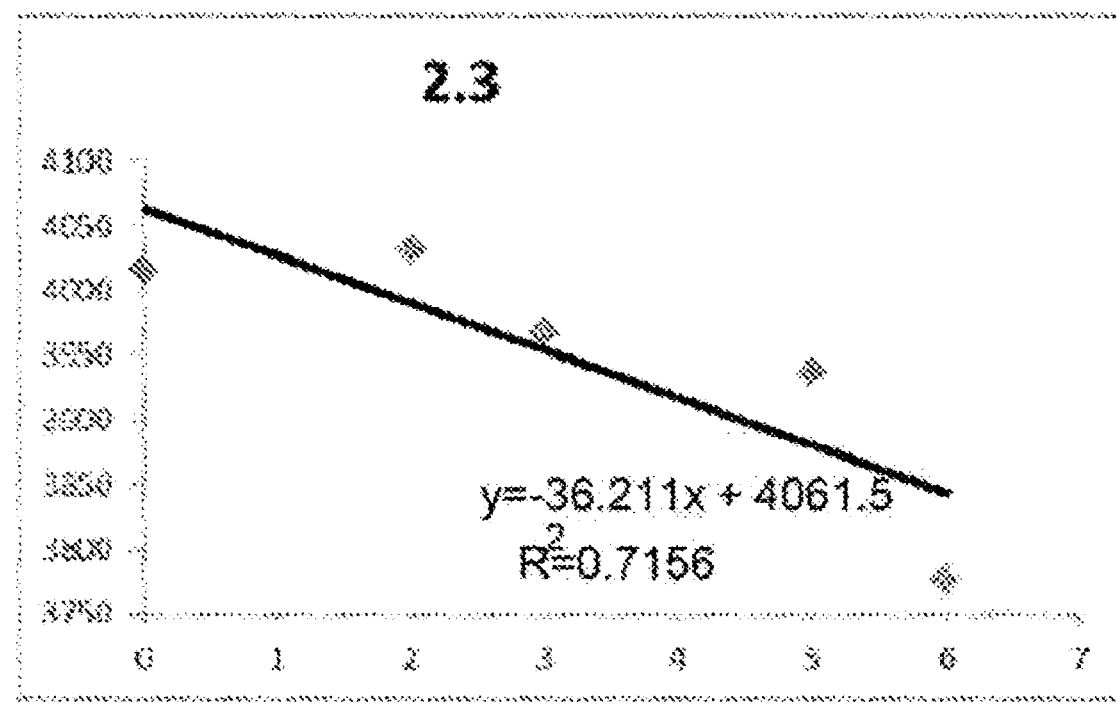
Figure 4G:
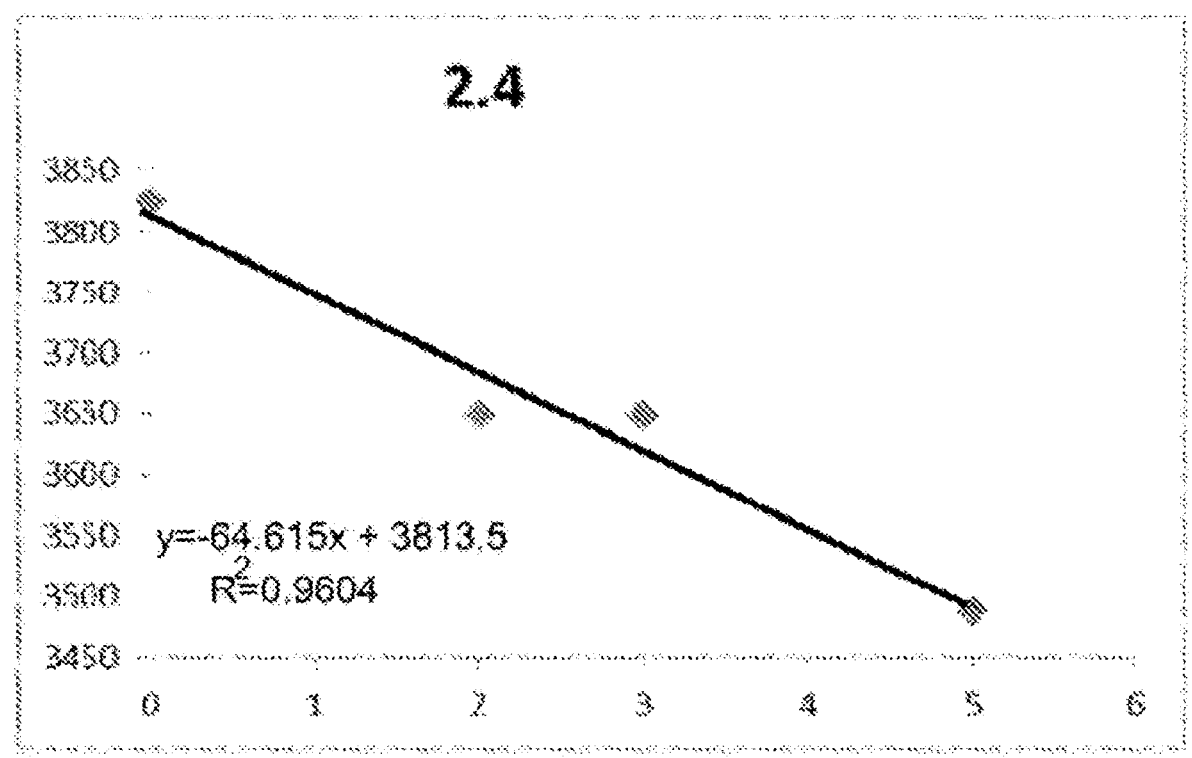

| | | | | |
|---|---|---|---|---|
| | 5 | 69 | | |
| | 6 | 58 | | |
| | 7 | 66 | | |
| | 8 | 59 | | |
| 2.2 and FIG. 4E | 0 | 162 | −20.3929 | −0.45329 |
| | 1 | 131 | | |
| | 2 | 115.5 | | |
| | 3 | 126 | | |
| | 4 | 98 | | |
| | 5 | 48.5 | | |
| | 6 | 32.5 | | |
| 2.3 and FIG. 4F | 0 | 4016 | −36.2105 | −0.80488 |
| | 2 | 4032 | | |
| | 3 | 3968 | | |
| | 5 | 3936 | | |
| | 6 | 3776 | | |
| 2.4 and FIG. 4G | 0 | 3824 | −64.6154 | −1.43625 |
| | 2 | 3648 | | |
| | 3 | 3648 | | |
| | 5 | 3488 | | |

Example 2—Electroactive Culture Production

Electroactive cultures are generated by first obtaining approximately 5 gallons (19 liters) of municipal sewage effluent from the Village of Castleton on Hudson, N.Y., and stored on ice for approximately 24 hours. The effluent is then analyzed for iron, manganese, sulfite, phosphorus, calcium and protein concentrations. When any of the foregoing factors are deficient or present in excess, cell growth media containing 5 g/L sodium acetate at ~4 g/L COD; 5 g/L sodium chloride; 0.05 g/L calcium chloride; 0.1 g/L iron chloride; 0.1 g/L casein peptone; 0.05 g/L iron(III)oxide; 0.01 g/L manganese(II)oxide; and 0.01 g/L cysteine hydrochloride is accordingly provided for stability and optimal cell proliferation. Thereafter, a stock of viable electrogenic cells and mixed culture bacteria (present in the wastewater effluent stream) are cultured for 21 days in the presence of an anionic electrode with an AMI-7001S anion exchange membrane, where a ferricyanide cathode is also employed. The culturing occurs in a temperature controlled environment at approximately 60° F. (15° C.) and the cells are monitored daily by using a multi-meter to track power and voltage fluctuations across 100Ω of external resistance. Should the voltage drop below 3 mV, media is replaced without disturbing the anode.

After 21 days of growth and maintenance, the cultures are harvested by manual scraping of the cultures from the electrode surfaces. The dry weight of the harvested culture is measured by obtaining vacuum-filtered scrapings (of the bacterial cells) from the anode and applying the cells to a filter disc of known weight. The filter disc and cells are then desiccated to remove water, thereby providing the dry weight of the cells. Material harvested from the electrode is subsequently concentrated by centrifugation using a Beckman centrifuge at 1500 RPM for 5 minutes. The resulting pellets are subsequently resuspended in cellular media supplemented with one or more growth factors as necessary, e.g., 30 uM ferric chloride, 1 mg/l hemoglobin, 0.5 uM $CaCl_2$, 10 ug/l cas-amino acids or molar equivalents of sulfur-containing amino acids, 0.5 uM selenium, and 12.5 ml/l of trace metal solution (1.5 g NTA, 3 g $MgSO_4$, 0.5 g $MnSO_4*H_2O$, 1 g NaCl, 0.1 g $FeSO_4*7 H_2O$, 0.1 g $CaCl_2*2 H_2O$, 0.1 g $CoCl_2*6 H_2O$, 0.01 g $AlK(SO_4)_2*12 H_2O$, 0.01 g $H_3BO_3$, 0.025 g $Na_2MoO_4$, 0.024 g $NiCl_2*6 H_2O$, 0.025 g $Na_2WO_4*2 H_2O$).

A standard inkjet printer is then reconfigured for cell printing—by removing the ink containing sponge and rinsing with 90% isopropyl alcohol, followed by water washes—and the resuspended cells are added to the sterile inkjet cartridge and the cover is replaced. Thereafter, the cells are printed onto an electrode circumferentially covered in carbon mesh. Finally, the electrode containing the printed cell application is ready for use or shipment.

All references cited herein are incorporated by reference in their entireties and for all purposes to the same extent as if each individual publication, patent, or patent application was specifically and individually incorporated by reference in its entirety for all purposes.

What is claimed is:

1. A method for producing bacteria for an electroactive biofilm, comprising
   forming a culture of electrogenic bacteria on an electrically conductive substrate wherein the culture possesses a culture bioconductance, and
   desiccating the culture of electrogenic bacteria to form a preserved culture.

2. The method of claim 1, further comprising harvesting the culture of electrogenic bacteria before desiccating.

3. The method of claim 2, further comprising applying the preserved culture to an electrode surface to form a biofilm.

4. The method of claim 3, wherein the biofilm possesses a biofilm bioconductance that is higher than the culture bioconductance.

5. The method of claim 1, further comprising conditioning the culture of electrogenic bacteria by adding a transfer mediator to the culture of electrogenic bacteria before desiccating the culture of electrogenic bacteria, wherein the transfer mediator is selected from the group consisting of $CaCl_2$), sulfur, cell growth medium, cell proliferation factors, cell adherence factors, and cell viability factors.

6. The method of claim 5, further comprising adding a quorum-sensing inducer to the culture of electrogenic bacteria before desiccating the culture of electrogenic bacteria.

7. The method of claim 1, wherein desiccating comprises freezing.

8. The method of claim 2, wherein the harvesting comprises collecting particles comprising surfaces and the electronic bacteria, wherein the electronic bacteria are on the surfaces of the particles.

9. The method of claim 8, further comprising applying the particles to an electrode surface to form a biofilm.

10. The method of claim 2, wherein desiccating comprises freezing.

11. The method of claim 10, wherein the harvesting comprises collecting particles comprising surfaces and the electronic bacteria, wherein the electronic bacteria are on the surfaces of the particles.

12. The method of claim 11, further comprising applying the particles to an electrode surface to form a biofilm.

13. The method of claim 3, wherein desiccating comprises freezing.

14. The method of claim 13, wherein the harvesting comprises collecting particles comprising surfaces and the electrogenic bacteria, wherein the electronic bacteria are on the surfaces of the particles.

15. The method of claim 14, further comprising applying the particles to an electrode surface to form a biofilm.

16. The method of claim 4, wherein desiccating comprises freezing.

17. The method of claim 16, wherein the harvesting comprises collecting particles comprising surfaces and the electrogenic bacteria, wherein the electronic bacteria are on the surfaces of the particles.

18. The method of claim 17, further comprising applying the particles to an electrode surface to form a biofilm.

19. The method of claim 8, further comprising conditioning the culture of electrogenic bacteria by adding a transfer mediator to the culture of electrogenic bacteria before desiccating the culture of electrogenic bacteria, wherein the transfer mediator is selected from the group consisting of $CaCl_2$), sulfur, cell growth medium, cell proliferation factors, cell adherence factors, and cell viability factors.

20. The method of claim 19, further comprising adding a quorum-sensing inducer to the culture of electrogenic bacteria before desiccating the culture of electrogenic bacteria.

21. The method of claim 7, wherein freezing comprises flash freezing in liquid nitrogen or slow freezing in the presence of glycerol.

22. The method of claim 10, wherein freezing comprises flash freezing in liquid nitrogen or slow freezing in the presence of glycerol.

\* \* \* \* \*

UNITED STATES PATENT AND TRADEMARK OFFICE
CERTIFICATE OF CORRECTION

PATENT NO. : 10,522,861 B2
APPLICATION NO. : 15/830580
DATED : December 31, 2019
INVENTOR(S) : Brent A. Solina Page 1 of 1

It is certified that error appears in the above-identified patent and that said Letters Patent is hereby corrected as shown below:

On the Title Page

In the Related U.S. Application Data (63): Delete "PCT/US2014/023185 on Mar. 14, 2014" and insert -- PCT/US2014/023185 on Mar. 11, 2014 --

Signed and Sealed this
Twentieth Day of October, 2020

Andrei Iancu
*Director of the United States Patent and Trademark Office*